(12) United States Patent
Cheresh et al.

(10) Patent No.: US 9,242,000 B2
(45) Date of Patent: Jan. 26, 2016

(54) MICRO-RNAS AND MICRO-RNA INHIBITORS TO MODULATE BLOOD VESSEL GROWTH, PATTERNING, TUMOR GROWTH AND MALIGNANT DISEASE AND METHOD FOR MAKING AND USING THEM

(71) Applicant: THE REGENTS OF THE UNIVERSITY OF CALIFORNIA, Oakland, CA (US)

(72) Inventors: David Cheresh, Encinitas, CA (US); Sudarshan Anand, San Diego, CA (US); Sunil Advani, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/057,235

(22) Filed: Oct. 18, 2013

(65) Prior Publication Data
US 2014/0127284 A1 May 8, 2014

Related U.S. Application Data

(60) Provisional application No. 61/715,422, filed on Oct. 18, 2012.

(51) Int. Cl.
*C12N 15/113* (2010.01)
*A61K 45/06* (2006.01)
*A61K 31/713* (2006.01)

(52) U.S. Cl.
CPC ............ *A61K 45/06* (2013.01); *A61K 31/713* (2013.01); *C12N 15/113* (2013.01); *C12N 2310/113* (2013.01); *C12N 2310/14* (2013.01); *C12N 2310/141* (2013.01)

(58) Field of Classification Search
None
See application file for complete search history.

(56) References Cited

U.S. PATENT DOCUMENTS

2008/0166344 A1* 7/2008 Nakahara et al. .......... 424/133.1

OTHER PUBLICATIONS

Yamakuchi et al. PNAS 2010, vol. 107, pp. 6334-6339.*
Finnerty et al. J. Mol. Biol. 2010, vol. 402, pp. 491-509.*

* cited by examiner

*Primary Examiner* — Tracy Vivlemore
(74) *Attorney, Agent, or Firm* — Gregory P. Einhorn; Greer Burns & Crain Ltd.

(57) ABSTRACT

In alternative embodiments, the invention provides compositions and methods comprising use of microRNAs and microRNA inhibitors to modulate blood vessel growth (angiogenesis), e.g., act as anti-angiogenic agents, and modulate cell and tumor microenvironment patterning, cancer cell and tumor growth and malignant disease (metastasis). In alternative embodiments, the invention provides compositions and methods that can sensitize blood vessels, e.g., tumor blood vessels, to radiation and agents and chemotherapies that cause DNA damage.

20 Claims, 22 Drawing Sheets

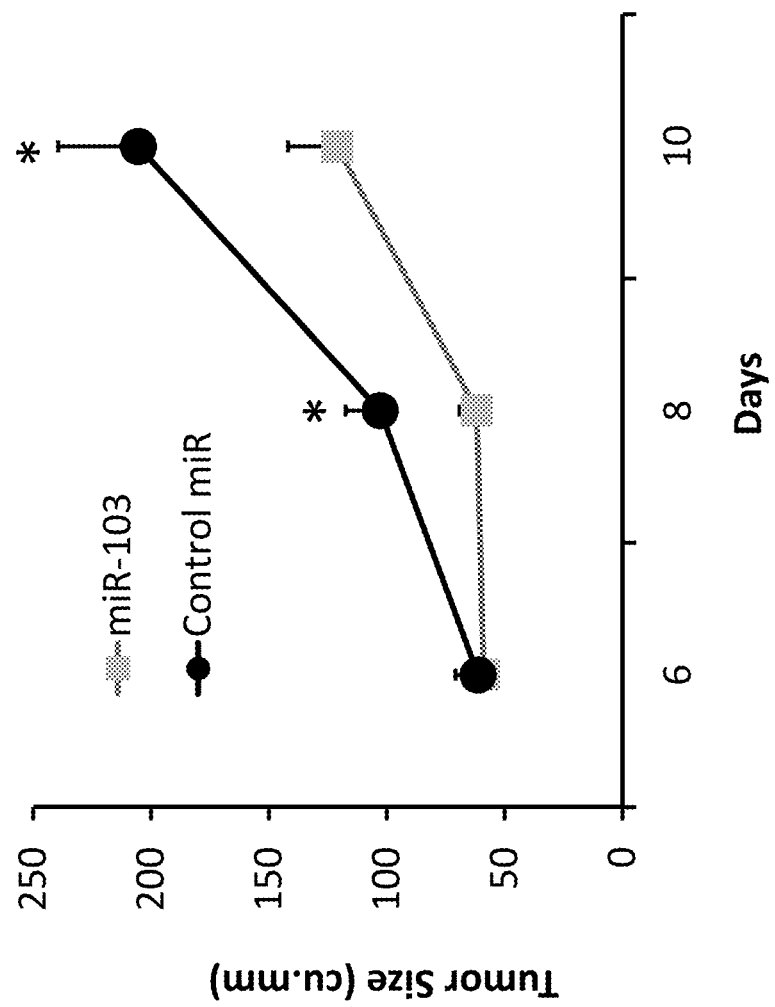

SEQUENCE LISTING

<160> NUMBER OF SEQ ID NOS: 2

<210> SEQ ID NO 1
<211> LENGTH: 23
<212> TYPE: RNA
<213> ORGANISM: artificial sequence

```
-continued

<220> FEATURE:
<223> OTHER INFORMATION: synthetic oligonucleotide

<400> SEQUENCE: 1
agcagcauug uacagggcua uga                                              23

<210> SEQ ID NO 2
<211> LENGTH: 62
<212> TYPE: DNA
<213> ORGANISM: artificial sequence
<220> FEATURE:
<223> OTHER INFORMATION: synthetic oligonucleotide

<400> SEQUENCE: 2
tcatagccct gtacaatgct gcttgatcca tatgcaacaa ggcagcactg taaagaagcc      60
ga                                                                     62
```

US 9,242,000 B2

MICRO-RNAS AND MICRO-RNA INHIBITORS TO MODULATE BLOOD VESSEL GROWTH, PATTERNING, TUMOR GROWTH AND MALIGNANT DISEASE AND METHOD FOR MAKING AND USING THEM

RELATED APPLICATIONS

This application claims the benefit of priority to U.S. Provisional Patent Application Ser. No. 61/715,422, filed Oct. 18, 2012. The aforementioned application is expressly incorporated herein by reference in its entirety and for all purposes.

GOVERNMENT RIGHTS

This invention was made with government support under grant number HL103956 awarded by the National Institutes of Health (NIH). The government has certain rights in the invention.

TECHNICAL FIELD

This invention generally relates to cell and molecular biology, diagnostics and oncology. In alternative embodiments, the invention provides compositions and methods comprising use of microRNAs and microRNA inhibitors to modulate blood vessel growth (angiogenesis), e.g., act as anti-angiogenic agents, and modulate cell and tumor microenvironment patterning, cancer cell and tumor growth and malignant disease (metastasis). In alternative embodiments, the invention provides compositions and methods that can sensitize blood vessels, e.g., tumor blood vessels, to radiation and agents and chemotherapies that cause DNA damage.

BACKGROUND

Endothelial cells in the adult mammal are among the least proliferative cell types, with about one in 10,000 cells entering the cell cycle at any given time. This quiescence is rapidly reversed in response to growth factors during pathological neovascularization, particularly during tumorigenesis. The robust proliferative switch of the quiescent endothelium is a complex process that is governed by a network of checks and balances. Small 22-nt RNAs called miRNAs are key regulators of several physiological processes, including angiogenesis.

The miR-103 microRNA precursor (homologous to miR-107), is a short non-coding RNA gene involved in gene regulation. miR-103 and miR-107 have now been predicted or experimentally confirmed in human. microRNAs are transcribed as approximately 70 nucleotide precursors and subsequently processed by the Dicer enzyme to give an approximately 22 nucleotide product. In this case the mature sequence comes from the 5' arm of the precursor. The mature products are thought to have regulatory roles through complementarity to mRNA.

mir-103 and mir-107 were noted as being upregulated in obese mice and were subsequently found to have a key role in insulin sensitivity. This lead to a suggestion that these microRNAs represent potential targets for the treatment of type 2 diabetes. mir-103 has also been linked with chronic pain and intestinal cell proliferation.

Trex1 exonuclease degrades ssDNA to prevent chronic checkpoint activation and autoimmune disease. C-terminal truncations in human 3'-5' DNA exonuclease TREX1 cause autosomal dominant retinal vasculopathy with cerebral leukodystrophy. In Cerebroretinal Vasculopathy, less TREX1 results in less blood vessels; and the disease manifestations begin during the fourth or fifth decade and there is 100% mortality over a 5 to 10 year period.

SUMMARY

In alternative embodiments, the invention provides compositions (e.g., kits, pharmaceutical formulations) and methods for regulating or modulating new blood vessel growth, or neovascularization or angiogenesis, comprising
(1) (a) providing a composition comprising or consisting of:
(i) a microRNA-103 (miRNA-103) or equivalents thereof, including chemically modified and stabilized forms of miRNA-103, and/or a FANCF gene expression-inhibiting composition (including a FANCF gene expression-inhibiting microRNA or siRNA), or
(ii) an anti-microRNA (miRNA-103, or anti-miR103) directed against a microRNA-103 or equivalents thereof, including chemically modified and stabilized forms of anti-miR103; and
(b) administering a sufficient amount of the composition, microRNA-103 or anti-microRNA-103, and/or a FANCF gene expression-inhibiting composition (including a FANCF gene expression-inhibiting microRNA or siRNA), to regulate or modulate vascularization or neovascularization,
wherein administering microRNA-103 (miRNA-103, or miR103) or equivalents thereof, including chemically modified and stabilized forms of miR103, and/or a FANCF gene expression-inhibiting composition (including a FANCF gene expression-inhibiting microRNA or siRNA), decreases, slows, reverses, or blocks new blood vessel growth, neovascularization or angiogenesis,
wherein administering anti-microRNA (anti-miRNA-103, or anti-miR103) directed against a microRNA-103 or equivalents thereof, including chemically modified and stabilized forms of anti-miR103, increases new blood vessel growth, neovascularization or angiogenesis; or
(2) the method of (1), wherein the composition comprises a pharmaceutical composition administered in vivo;
(3) the method of (1) or (2), wherein the composition is administered intravenously (IV), or by vessel-targeted nanoparticle or liposome delivery; or
(4) the method of (1), (2) or (3), wherein administering microRNA-103 (miRNA-103, or miR103) or equivalents thereof, including chemically modified and stabilized forms of miR103, and/or a FANCF gene expression-inhibiting composition (including a FANCF gene expression-inhibiting microRNA or siRNA), in conjunction with standard genotoxic chemotherapies, cancer cell chemotherapies or treatments, or radiation and the like or equivalents, achieves enhanced killing of endothelial cells and decreased angiogenesis, pathologic angiogenesis, or tumor angiogenesis.

In alternative embodiments, administering microRNA 103 (miRNA-103) or equivalents thereof, including chemically modified and stabilized forms of miR103, and/or a FANCF gene expression-inhibiting composition (including a FANCF gene expression-inhibiting microRNA or siRNA), decreases, slows, reverses or blocks or reverses new blood vessel growth, neovascularization or angiogenesis, and treats, prevents or ameliorates conditions that are responsive to blocking or slowing or reversing the development of neovascularization or new blood vessels, which optionally reduces, treats, prevents or ameliorates the level of disease in a retinal age-related macular degeneration, a diabetic retinopathy, a cancer, a glioblastoma, a neuroma, a neuroblastoma, a colon carcinoma, a hemangioma, an infection and/or a condition with at least one inflammatory component, and/or any infectious or inflammatory disease, such as a rheumatoid arthritis, a psoriasis, a fibrosis, or leprosy.

In alternative embodiments, administering an anti-microRNA-103 (anti-miRNA-103) or equivalents thereof, including chemically modified and stabilized forms of anti-miR103, increases new blood vessel growth, neovascularization or angiogenesis, treats, reverses, prevents or ameliorates conditions and diseases associated with ischemia, including myocardial infarction (MI, or heart attack); ischemic disease; thrombotic disease; stroke; limb, organ or tissue transplantation or limb reattachment; trauma; injury; and/or an ulcer or a diabetic ulcer.

In alternative embodiments, the invention provides compositions (e.g., kits, pharmaceutical formulations) and methods for treating, reversing, preventing or ameliorating a condition or disease associated with an ischemia; a myocardial infarction (MI, or heart attack); an ischemic disease; a thrombotic disease; a stroke; a limb, organ or tissue transplantation or a limb reattachment; a trauma; an injury; and/or an ulcer or a diabetic ulcer, comprising
(1)
(a) providing a composition comprising or consisting of an anti-microRNA (anti-miRNA-103, or anti-miR103) directed against a microRNA-103 or equivalents thereof, including chemically modified and stabilized forms of anti-miR103; and
(b) administering a sufficient amount of the composition, anti-microRNA-103 or equivalents thereof, wherein administering anti-microRNA (anti miRNA 301, or anti-miR103) or equivalents thereof directed against a microRNA-103, including chemically modified and stabilized forms of anti-miR103, treats, reverses, prevents or ameliorates the condition or disease associated with the ischemia; myocardial infarction (MI, or heart attack); ischemic disease; thrombotic disease; stroke; limb, organ or tissue transplantation or limb reattachment; trauma; injury; and/or ulcer or diabetic ulcer; or
(2) the method of (1), wherein the composition comprises a pharmaceutical composition administered in vivo; or
(3) the method of (1) or (2), wherein the composition is administered intravenously (IV), or by vessel-targeted nanoparticle or liposome delivery.

In alternative embodiments, the invention provides compositions (e.g., kits, pharmaceutical formulations) and methods for reducing, preventing, reversing, treating or ameliorating the level of disease in a retinal age-related macular degeneration, a diabetic retinopathy, a cancer, a glioblastoma, a neuroma, a neuroblastoma, a colon carcinoma, a hemangioma, an infection; a condition with at least one inflammatory component; an infectious or an inflammatory disease; a rheumatoid arthritis; a psoriasis; a fibrosis; and/or leprosy, comprising
(1) (a) providing a composition comprising or consisting of a microRNA-103 (miRNA-103, or miR103) or equivalents thereof, including chemically modified and stabilized forms of miR103, and/or a FANCF gene expression-inhibiting composition (including a FANCF gene expression-inhibiting microRNA or siRNA); and
(b) administering a sufficient amount of the composition, microRNA-103 or equivalents, and/or a FANCF gene expression-inhibiting composition (including a FANCF gene expression-inhibiting microRNA or siRNA), to reduce, prevent, reverse, treat or ameliorate the level of disease in the retinal age-related macular degeneration, diabetic retinopathy, cancer, glioblastoma, neuroma, neuroblastoma, colon carcinoma, hemangioma, infection and/or condition with at least one inflammatory component; infectious or inflammatory disease; rheumatoid arthritis; psoriasis; fibrosis; and/or leprosy; or
(2) the method of (1), wherein the composition comprises a pharmaceutical composition administered in vivo; or
(3) the method of (1) or (2), wherein the composition is administered intravenously (IV), or by vessel-targeted nanoparticle or liposome delivery.

In alternative embodiments, the invention provides compositions (e.g., kits, pharmaceutical formulations) and methods for: inhibiting DNA repair enzymes TREX1 and TREX2, or destabilizing a DNA repair response of a cell, or forcing or stimulating a cell to undergo cell cycle arrest or cell death, comprising:
(1) (a) providing a composition comprising or consisting of a microRNA-103 (miRNA-103, or miR103) or equivalents thereof, including chemically modified and stabilized forms of microRNA-103, and/or a FANCF gene expression-inhibiting composition (including a FANCF gene expression-inhibiting microRNA or siRNA); and
(b) administering a sufficient amount of the composition, microRNA-103 or equivalents, and/or a FANCF gene expression-inhibiting composition (including a FANCF gene expression-inhibiting microRNA or siRNA), to inhibit DNA repair enzymes TREX1 and TREX2, or destabilize a DNA repair response of a cell, or force or stimulate a cell to undergo cell cycle arrest or cell death;
(2) the method of (1), wherein the composition comprises a pharmaceutical composition administered in vivo; or
(3) the method of (1) or (2), wherein the composition is administered intravenously (IV), or by vessel-targeted nanoparticle or liposome delivery.

In alternative embodiments, the invention provides methods for sensitizing cells, endothelial cells or blood vessel cells to a radiation or a radiation therapy, or a genotoxic agent or a chemotherapy, comprising
(1) (a) providing a composition comprising or consisting of: a microRNA-103 (miR103) or equivalents thereof, including chemically modified and stabilized forms of miRNA-103, and/or a FANCF gene expression-inhibiting composition (including a FANCF gene expression-inhibiting microRNA or siRNA), and
(b) administering a sufficient amount of the composition or microRNA-103 and/or a FANCF gene expression-inhibiting composition (including a FANCF gene expression-inhibiting microRNA or siRNA), to sensitize the cells to the radiation or radiation therapy, or genotoxic agent or chemotherapy,
wherein administering microRNA-103 (miRNA-103, or miR103) or equivalents thereof, includes chemically modified and stabilized forms of miR103 and/or a FANCF gene expression-inhibiting composition (including a FANCF gene expression-inhibiting microRNA or siRNA); or
(2) the method of (1), wherein the composition comprises a pharmaceutical composition administered in vivo;
(3) the method of (1) or (2), wherein the composition is administered intravenously (IV), or by vessel-targeted nanoparticle or liposome delivery;
(4) the method of (1), (2) or (3), wherein administering microRNA-103 (miRNA-103, or miR103) or equivalents thereof, including chemically modified and stabilized forms of miR103, and/or a FANCF gene expression-inhibiting composition (including a FANCF gene expression-inhibiting microRNA or siRNA), in conjunction with standard genotoxic chemotherapies, cancer cell chemotherapies or treatments, or radiation and the like or equivalents, achieves enhanced killing of endothelial cells and decreased angiogenesis, pathologic angiogenesis, or tumor angiogenesis; or (5) the method of any of (1) to (4), wherein the microRNA-103 and/or a FANCF gene expression-inhibiting composition (including a FANCF gene expression-inhibiting microRNA or siRNA), is administered before, during and/or after the genotoxic chemotherapy, cancer cell chemotherapy or treatment, or radiation treatment or therapy and the like or equivalents.

In alternative embodiments, the invention provides methods for protecting cells, endothelial cells or blood vessel cells after their exposure to a radiation or a radiation therapy, or a genotoxic agent or a chemotherapy, comprising (1) (a) providing a composition comprising or consisting of:
an anti-microRNA (anti miRNA 301, or anti-miR103) directed against a microRNA-103 or equivalents thereof, including chemically modified and stabilized forms of anti-miR103; and
(b) administering a sufficient amount of the composition or anti-microRNA-103 to protect the cells, endothelial cells or blood vessel cells after their exposure to a radiation or a radiation therapy, or a genotoxic agent or a chemotherapy; or (2) the method of (1), wherein the composition comprises a pharmaceutical composition administered in vivo;

(3) the method of (1) or (2), wherein the composition is administered intravenously (IV), or by vessel-targeted nanoparticle or liposome delivery; or (4) the method of any of (1) to (3), wherein the anti-microRNA-103 is administered before, during and/or after the genotoxic chemotherapy, cancer cell chemotherapy or treatment, or radiation treatment or therapy and the like or equivalents.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments of the invention and are not meant to limit the scope of the invention as encompassed by the claims.

Like reference symbols in the various drawings indicate like elements.

In FIG. 4A, the top five (5) most upregulated microRNAs at 20 Gy are shown. The bar graph (FIG. 4B) graphically illustrates data from a real-time PCR for miR-103 after 6 hours treatment of endothelial cells with the indicated compounds.

FIG. 5A illustrates confocal imaging as performed typically on day 4 with a fluorescent lectin. FIG. 5B graphically illustrates bar graphs showing quantification of these endothelial sprouts (Area) using IMAGE J™ software (a public domain, Java-based image processing program developed at the National Institutes of Health). Conclusion: expression of miR-103 in endothelial cells decreases angiogenesis.

FIG. 6C graphically illustrates bar graphs showing quantification of these endothelial sprouts, and the conclusion is: inhibition of miR-103 using an anti-miR protects endothelial cells from death and rescues angiogenesis.

FIG. 9 is derived from and described in Kavanagh, et al., Cell Cycle. 2008 Jun. 15; 7(12): 1718-1725.

FIG. 10G, FIG. 10H, FIG. 10I illustrate drawings of fluorescein angiography and indocyanine green photographs of the retina show views of the macula of the right eye. Periarteriolar narrowing and sheathing, focal leakage, telangiectasias, and cotton wool spots are present. FIG. 10 is derived from and described in e.g., F. J. Mateen, et al. Neurology. 2010 Sep. 28; 75(13):1211-1213.

FIG. 11A is an illustration of the cells stained with an antibody to detect phospho-histone H2AX. Conclusion: miR-103 expression in cells increases the phosphorylation of histone H2AX and indicates increased DNA damage.

FIG. 15A illustrates confocal images of the deep plexus blood vessels in the retina; and FIG. 15B graphically illustrates the quantifying of this data; where the conclusion is that this model demonstrates that miR-103 injection works as an anti-angiogenic agent in a physiological vascular bed in the developing retina of mouse.

FIGS. 17A and 17D graphically illustrate the levels of: TREX1, TREX2 and FANCF (FIG. 17A), and TREX1 site A and B, and FANCF (FIG. 17B). Conclusion: miR-103 decreases mRNA and protein levels of FANCF, TREX1 and TREX2; and, miR-103 directly binds to the TREX1 and FANCF mRNAs.

FIG. 18A illustrates data from experiments where endothelial cells were treated with different stress reagents as shown, and six hours later RNA was extracted and real time PCR was performed to detect mIR-103. FIG. 18B illustrates data from real time PCR from different cell lines 6 hours after a high dose radiation. Conclusion: miR-103 is expressed in response to a variety of genotoxic stressors; it is upregulated in response to radiation in primary vascular and stromal cell types but not in specific tumor cells.

FIG. 20A illustrates data from experiments where endothelial cells were transfected as indicated, and 48 hours later, the cells were assayed for apoptosis by flow cytometry using antibodies to cleaved PARP and Caspase-3. FIG. 20B graphically illustrates this data. Conclusion: decrease of FANCF leads to increased endothelial cell death and decreased angiogenesis in the developing mouse retina.

FIG. 22 graphically illustrates data showing that the intravenous administration of miR-103 decreases tumor growth in vivo. Method: 1.5 million HCT-116 human colon carcinoma cells were injected into the flank of athymic nude mice. Tumors were measured on day 6 and mice were randomly assigned to two treatment groups: control microRNA or microRNA-103. Mice were injected with 100 micrograms of microRNA in saline intravenously on days 6, 8 and 10 and tumor size was measured using calipers. * indicates statistical significance at P<0.05 using two-tailed Student's t-test. Conclusion: This data indicates the intravenous administration of miR-103 decreases tumor growth.

Figure 1:
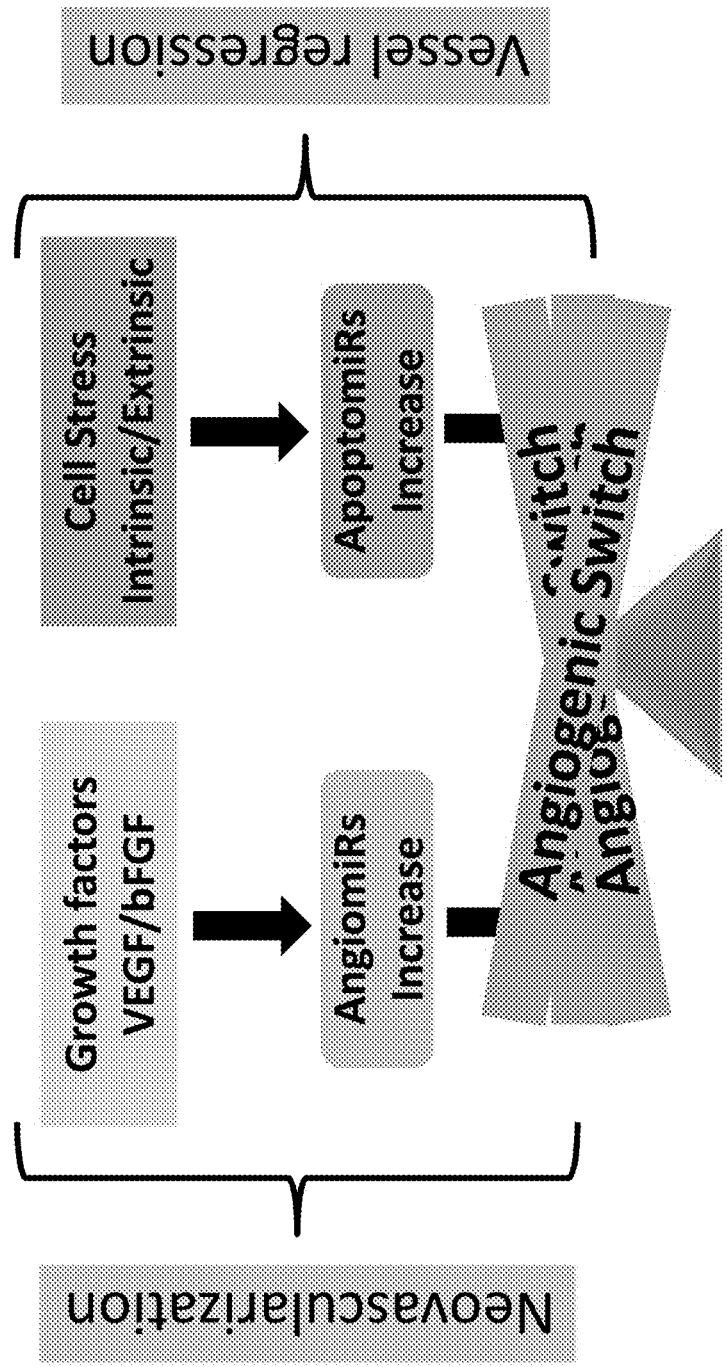
FIG. 1 illustrates how angiogenesis is controlled in vivo by a balance of 'angiomiRs' and 'apoptomiRs', and thus illustrates how practicing this invention can use the exemplary 'angiomiRs' and 'apoptomiRs' of the invention to change or manipulate this balance, for example, where methods or compositions of the invention are used to ameliorate or enhance intrinsic or extrinsic cell stressors; or where methods or compositions of the invention are used to begin, enhance or accelerate vascularization or neovascularization, or the cause endothelial cell regression or death.
Figure 2:
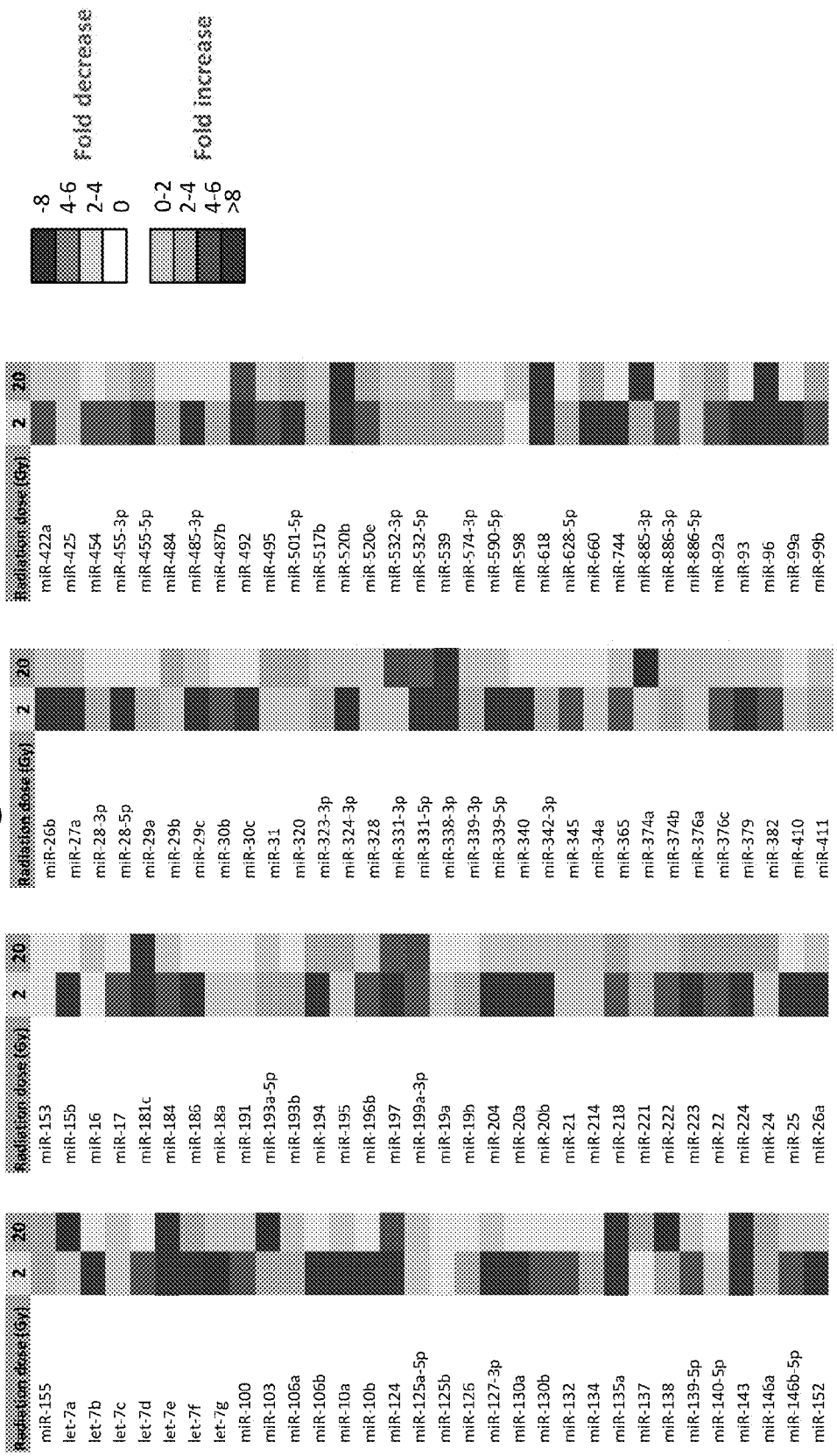
FIG. 2 graphically illustrates data showing how genotoxic stress, radiation (where radiation doses were 2 and 20 Gy) (gray (symbol: Gy) is the International System of Units (SI) derived unit of absorbed dose, specific energy (imparted) and of kerma) causes dose dependent global dysregulation of miRs.
Figure 3:
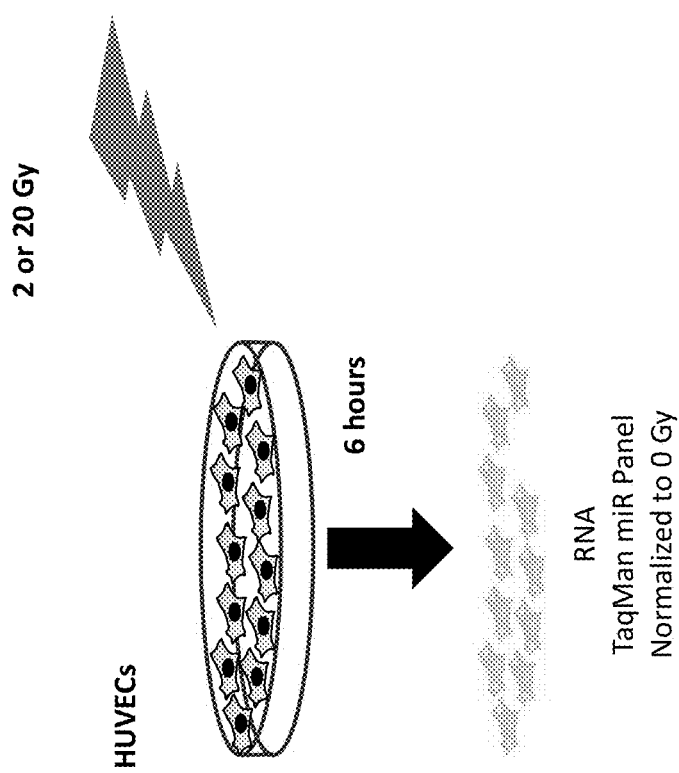
FIG. 3 schematically illustrates how the data of FIG. 2 was generated, briefly, human endothelial cells were treated with different doses of radiation (0, 2, 20 Gy). Six (6) hours later, RNA was isolated, reverse transcribed and real-time PCR was performed on TAQMAN™ microfluidic cards (Life Technologies, Carlsbad, Calif.) that contain 384 reaction wells each with a unique miR probe. The heatmap of FIG. 2, depicts the differential expression of microRNAs upon radiation normalized to the no radiation group 0 Gy group. Conclusion: radiation induces significant changes in expression of endothelial microRNAs.
Figure 4:
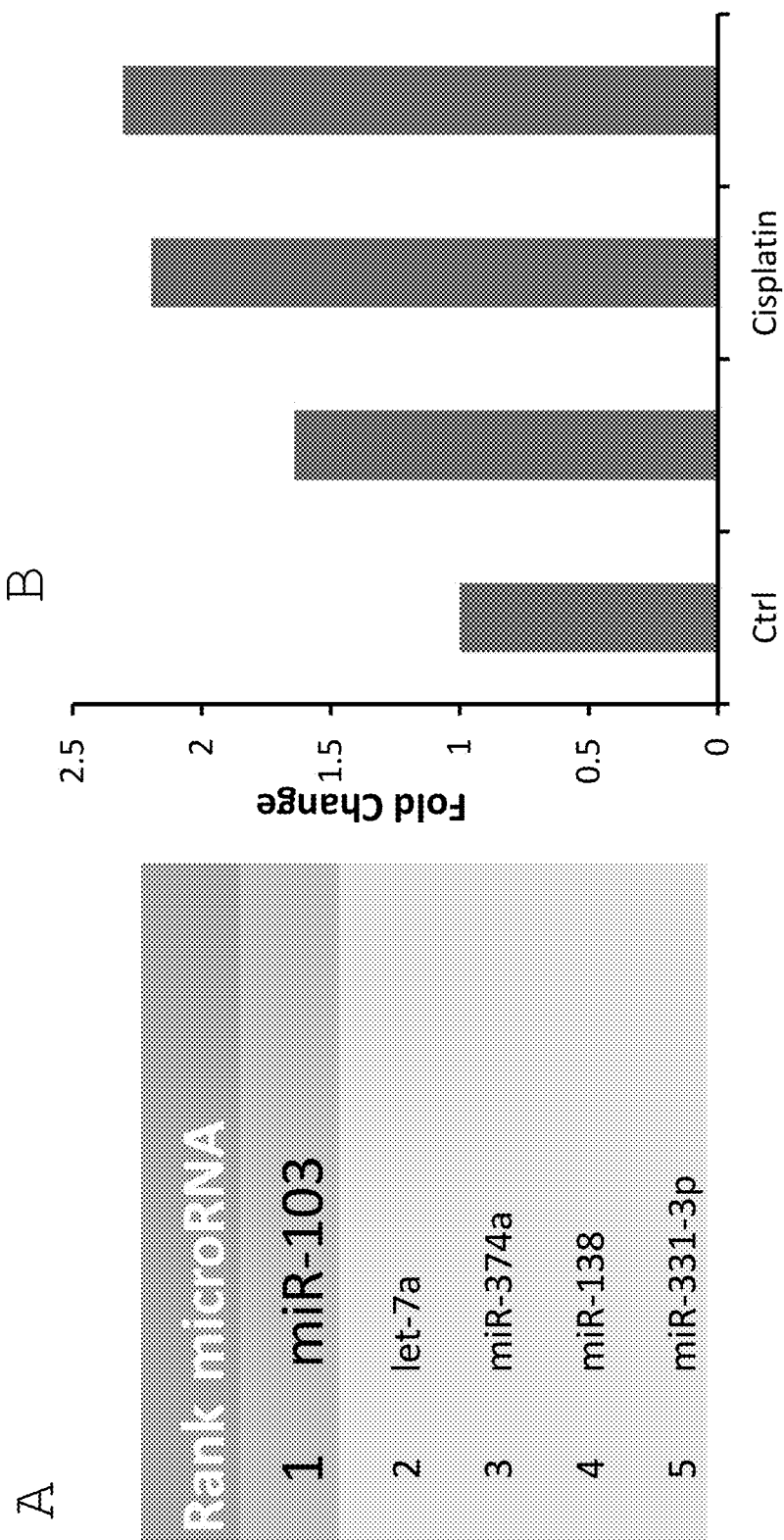
FIG. 4 graphically illustrates data showing that miR-103 is the most upregulated miR in response to diverse stress stimuli in endothelial cells. The ranking table (FIG. 4A) is based on the data illustrated in FIG. 2.
Figure 5:
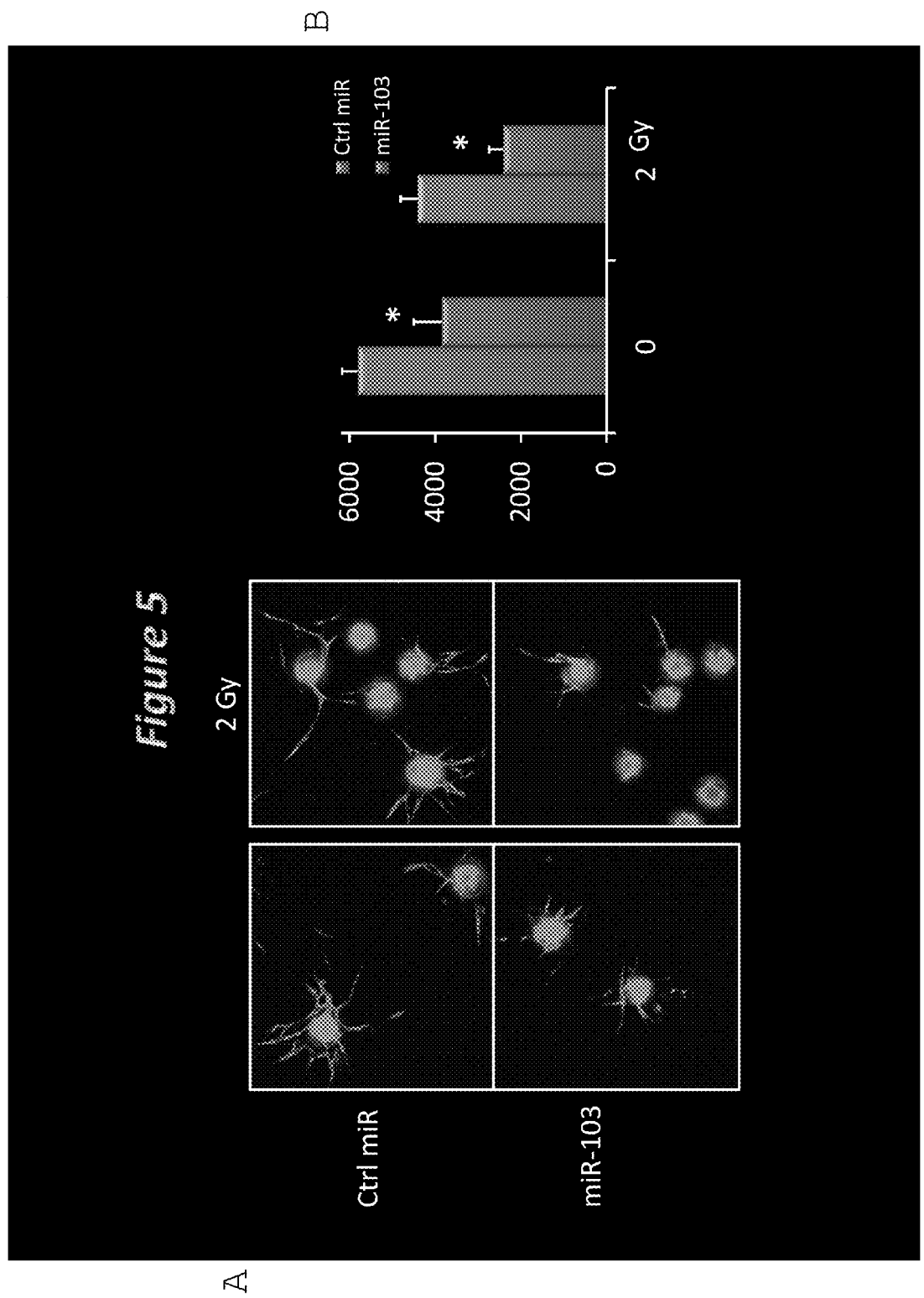
FIG. 5 graphically illustrates data showing that ectopic expression of miR-103 decreases tube formation and exacerbates genotoxic stress. Briefly, human endothelial cells were transfected with a control miR or miR-103 using RNAi MAX™ reagent (Life Technologies, Carlsbad, Calif.). Sixteen (16) hours later, one set of cells were irradiated with the indicated dose of radiation. Two (2) hours later, the cells were harvested and coated on CYTODEX™ beads (Sigma-Aldrich, St. Louis, Mo.) and allowed to adhere overnight. The beads were then suspended in a fibrin gel containing smooth muscle cells and allowed to undergo sprouting angiogenesis for 3-4 days.
Figure 6:
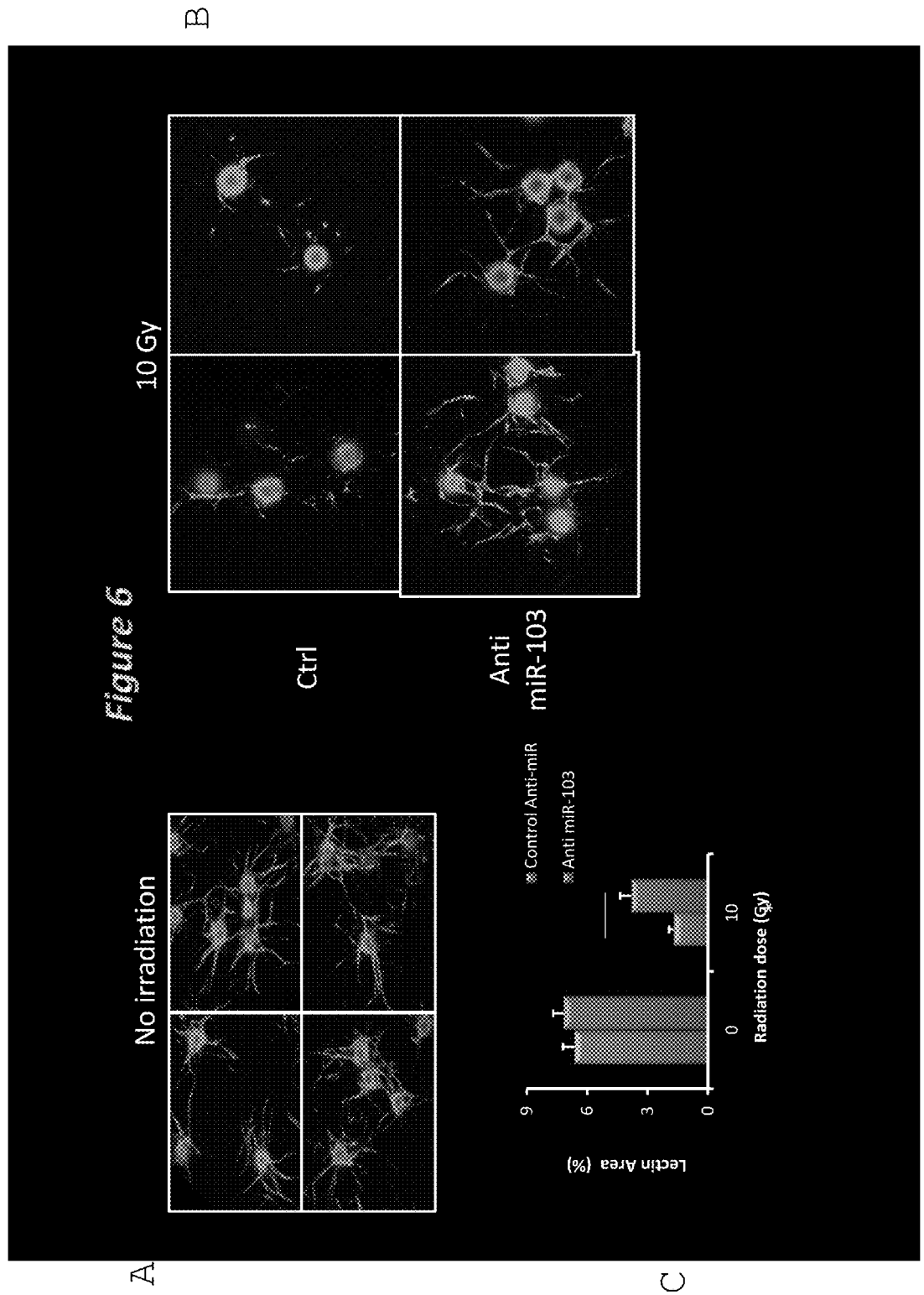
FIG. 6 graphically illustrates data showing that blockade of endothelial miR-103 (using anti-miR-103) rescues tube formation. In brief, sprouting assay were carried out as FIG. 5: where FIGS. 6A (control, no radiation) and 6B (having anti-miR-103) illustrate the confocal imaging results.
Figure 7:
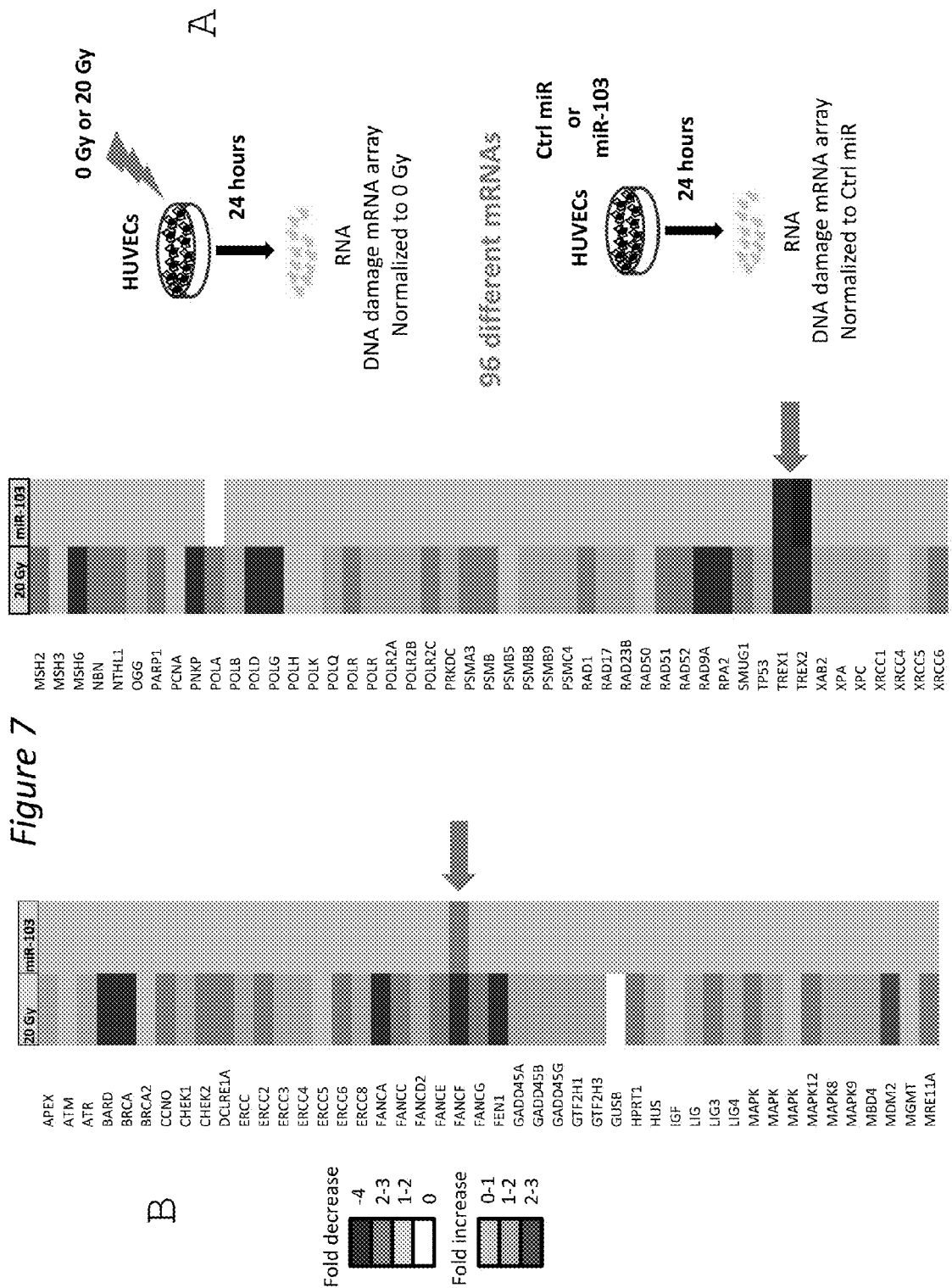
FIG. 7 graphically illustrates data showing that mRNA profiling identifies three (3) common targets down-regulated by both genotoxic stress and miR-103. In brief, the protocols are illustrated in FIG. 7A, where RNA isolated from endothelial cells (HUVECs) treated with radiation (0 or 20 Gy) or transfected with an miR-103 (one of the 96 species illustrated in FIG. 7A); real time PCR was performed on a 96 well DNA damage array. Results are graphically illustrated in FIG. 7A. Conclusion: only three "DNA damage" mRNAs, or FANCF, TREX 1 and TREX2, are regulated by both miR-103 and high dose radiation (the "Fanconi anemia group F", or FANCF, protein in humans is encoded by the FANCF gene; and, the "three prime repair exonuclease 1" is an enzyme that in humans is encoded by the TREX1 gene, and the "three prime repair exonuclease 2" is an enzyme that in humans is encoded by the TREX2 gene, and TREX is a major 3'->5' DNA exonuclease in human cells).
Figure 8:
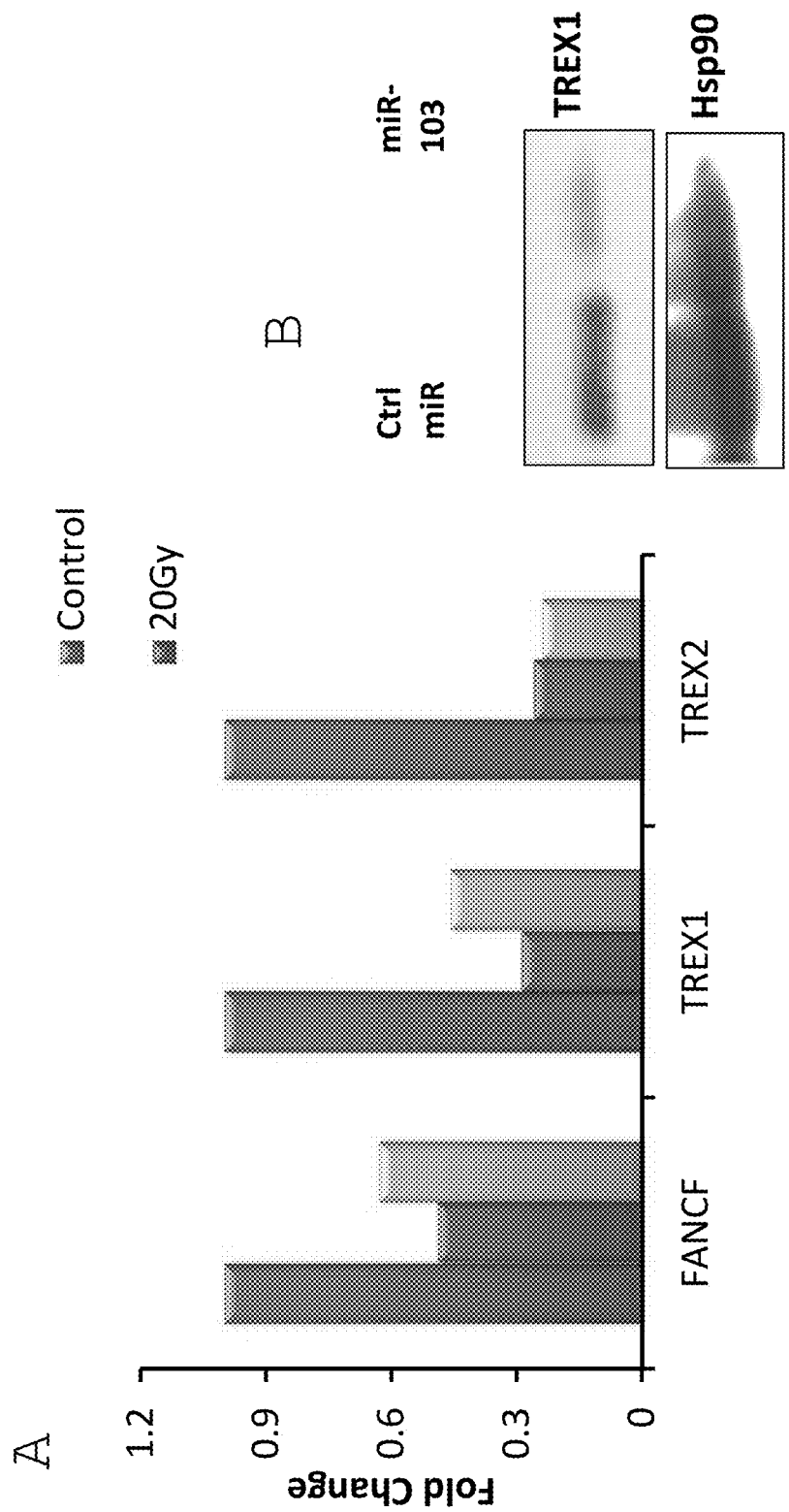
FIG. 8A graphically illustrates data showing that mRNA profiling identifies 3 common targets down-regulated by both genotoxic stress and miR-103. In brief, real-time PCR for the three target genes FANCF, TREX 1 and TREX2 identified as described for FIG. 7.
FIG. 8B illustrates a gel showing a decrease of TREX1 protein 24 hours after miR-103 transfection. Conclusion: expression of miR-103 or treatment of endothelial cells with radiation decreases mRNA levels of FANCF, TREX1 and TREX2, and expression of miR-103 decreases TREX1 protein levels.
Figure 9:
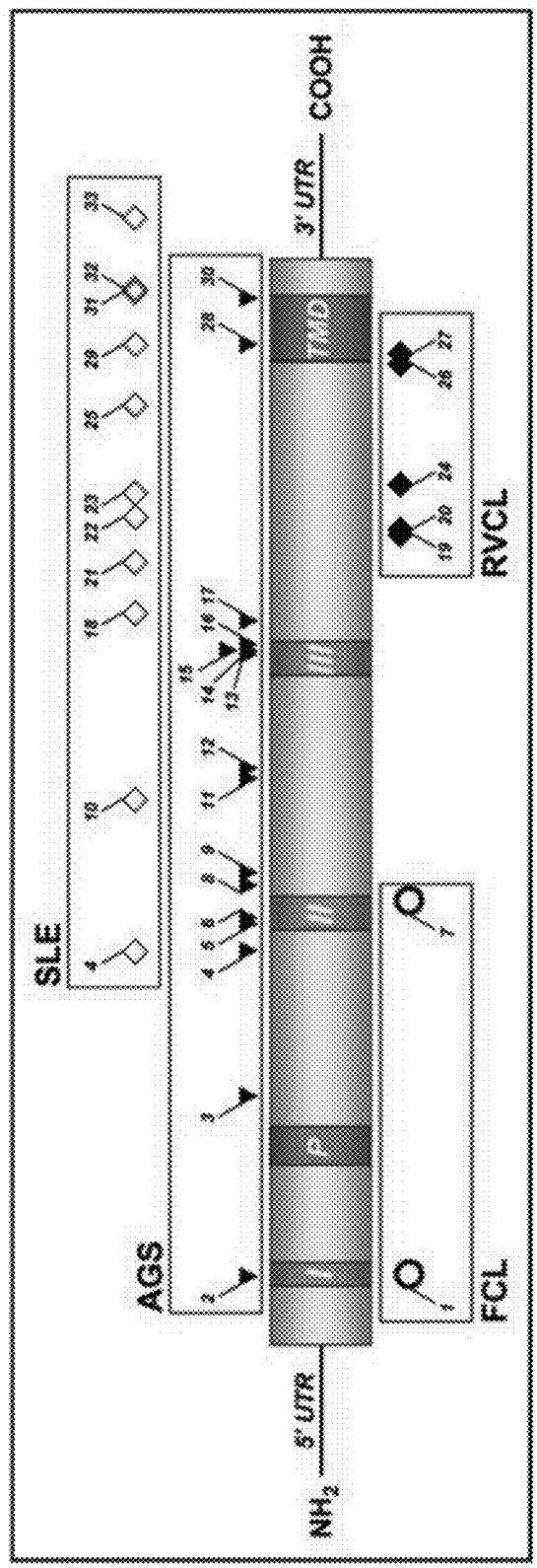
FIG. 9 schematically illustrates how several mutations, or polymorphisms, in TREX are associated with human diseases: Trex1 exonuclease degrades ssDNA to prevent chronic checkpoint activation and autoimmune disease; Trex1 prevents cell-intrinsic initiation of autoimmunity; C-terminal truncations in human 3'-5' DNA exonuclease TREX1 cause autosomal dominant retinal vasculopathy with cerebral leukodystrophy.
Figure 10:
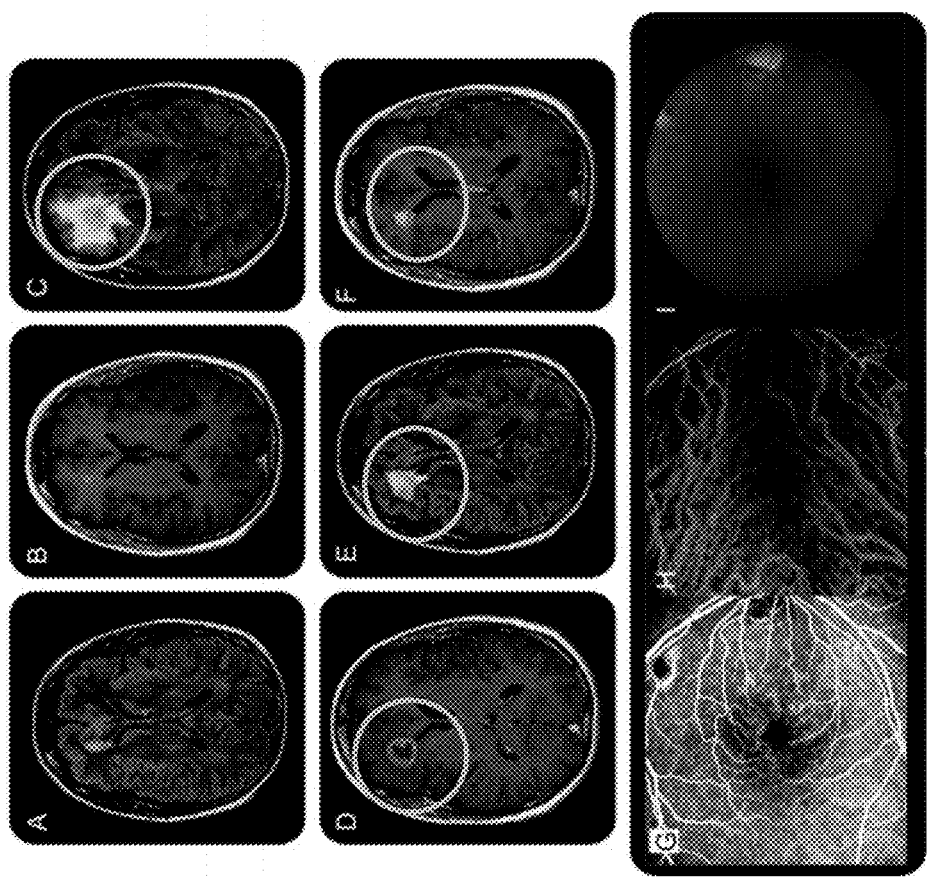
FIG. 10 illustrates brain and retinal imaging in a patient with cerebroretinal vasculopathy, and illustrates that mutations in TREX1 in humans causes Cerebroretinal Vasculopathy. The disease manifestations begin during the fourth or fifth decade and there is 100% mortality over a 5 to 10 year period. Less TREX1 results in less blood vessels; capillary dropouts in macula; loss of central vision; capillary obliteration; obliterative vasculopathy. Classic description of the histopathogenesis: "As if the brain had been irradiated". Sequential axial MRI showing an ovoid T2-hyperintense (FIG. 10A) and gadolinium-enhancing (FIG. 10B) lesion (2.1×1 cm), abutting the frontal horn of the right lateral ventricle, bright on both diffusion-weighted imaging (DWI) and apparent diffusion coefficient (ADC) map. At 6 months, a larger, more aggressive-appearing lesion (2×2×3 cm) with surrounding edema occupied the right frontal lobe. There was a central zone of presumed necrosis and gadolinium enhancement of the lesion rim (FIG. 10C, FIG. 10D). Diffusion imaging showed more heterogeneous signal, without the characteristic bright DWI and dark ADC signal of acute infarction. At 12 months, the lesion approximated its size on initial imaging (1.4×1.2×0.9 cm) with a persistent rim pattern of enhancement (FIG. 10E, FIG. 10F). At 18 months, the lesion further decreased in size (1.1×0.9×0.3 cm) with near resolution of the surrounding edema.
Figure 11:
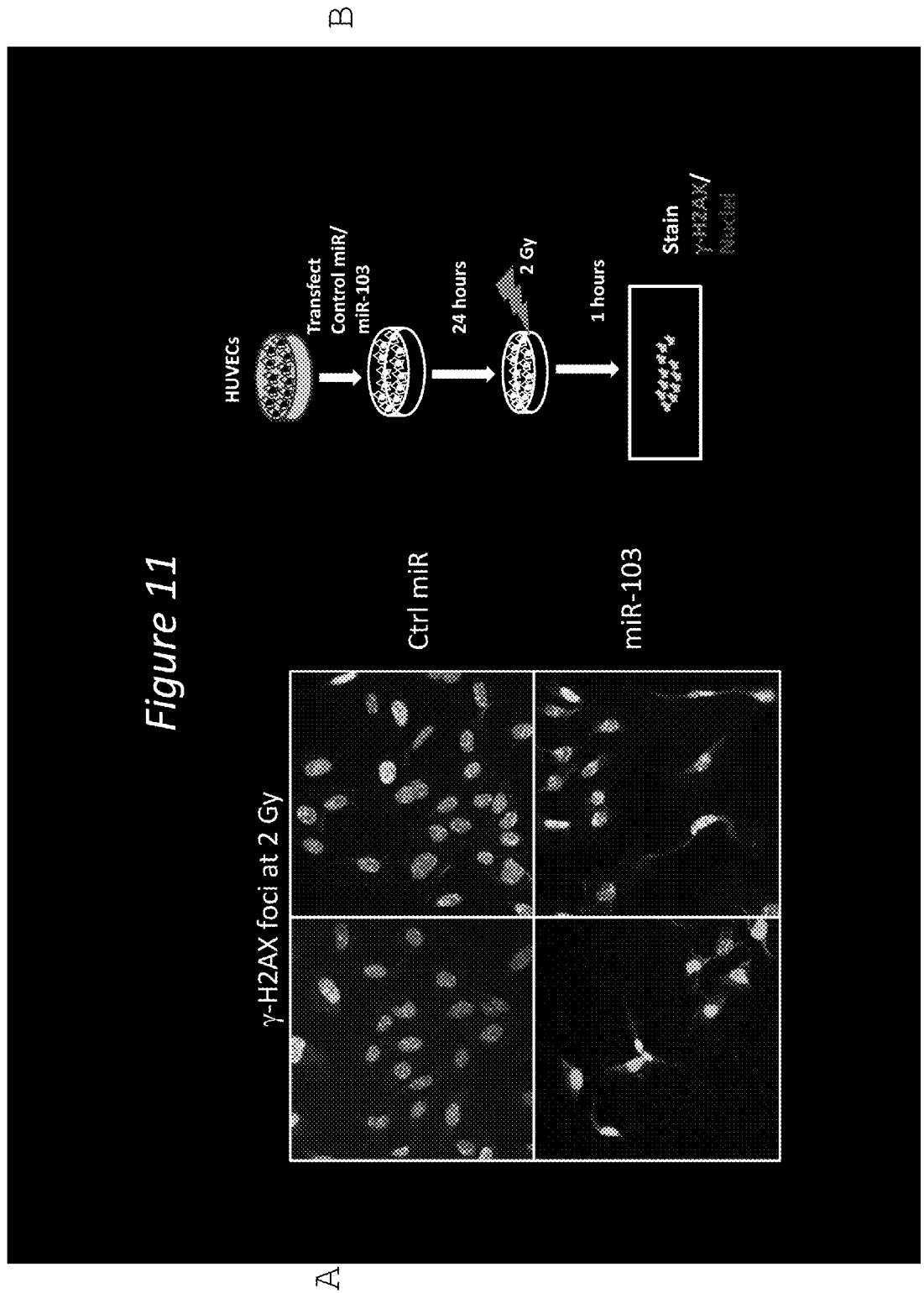
FIG. 11 illustrates that miR-103 exacerbates g-H2AX foci upon irradiation; Histone H2AX gets phosphorylated at sites of DNA double strand breaks, more DNA damage, of, that more miR-103 results in more g-H2AX foci. Histone H2AX gets phosphorylated at sites of DNA double strand breaks, and the more DNA damage the more g-H2AX. In brief, as illustrated in FIG. 11B, endothelial cells were transfected as described above, and irradiated 24 hours later (with 2 Gy); and then one hour after radiation, they were stained with an antibody to detect phospho-histone H2AX.
Figure 12:
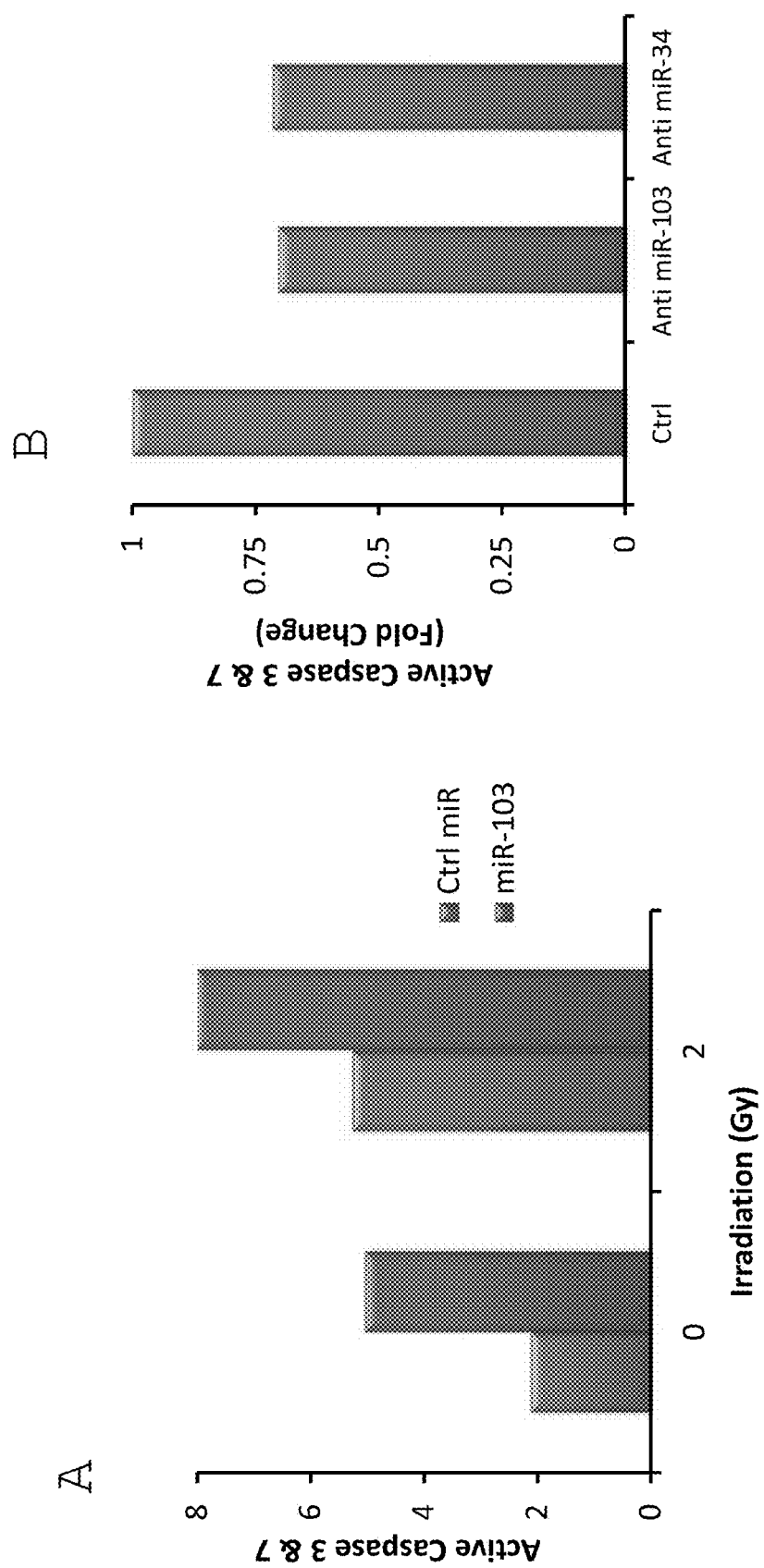
FIG. 12 graphically illustrates data showing that miR-103 (FIG. 12A) exacerbates while anti-miR (FIG. 12B) inhibits radiation induced endothelial apoptosis. Endothelial cells were transfected and irradiated as described above. 48 hours after radiation, apoptosis was measured by flow cytometry by using an active caspase probe, wherein the presence of caspase indicate apoptosis, i.e., the more caspase the higher the degree is apoptosis. Conclusion: Expression of miR-103 (FIG. 12A) increases apoptosis (more caspase) whereas inhibition of miR-103 (FIG. 12B) decreases apoptosis (less caspase). Inhibition of another miR (FIG. 12B), miR-34a, also identified in the screen described above, inhibits apoptosis (less caspase).
Figure 13:
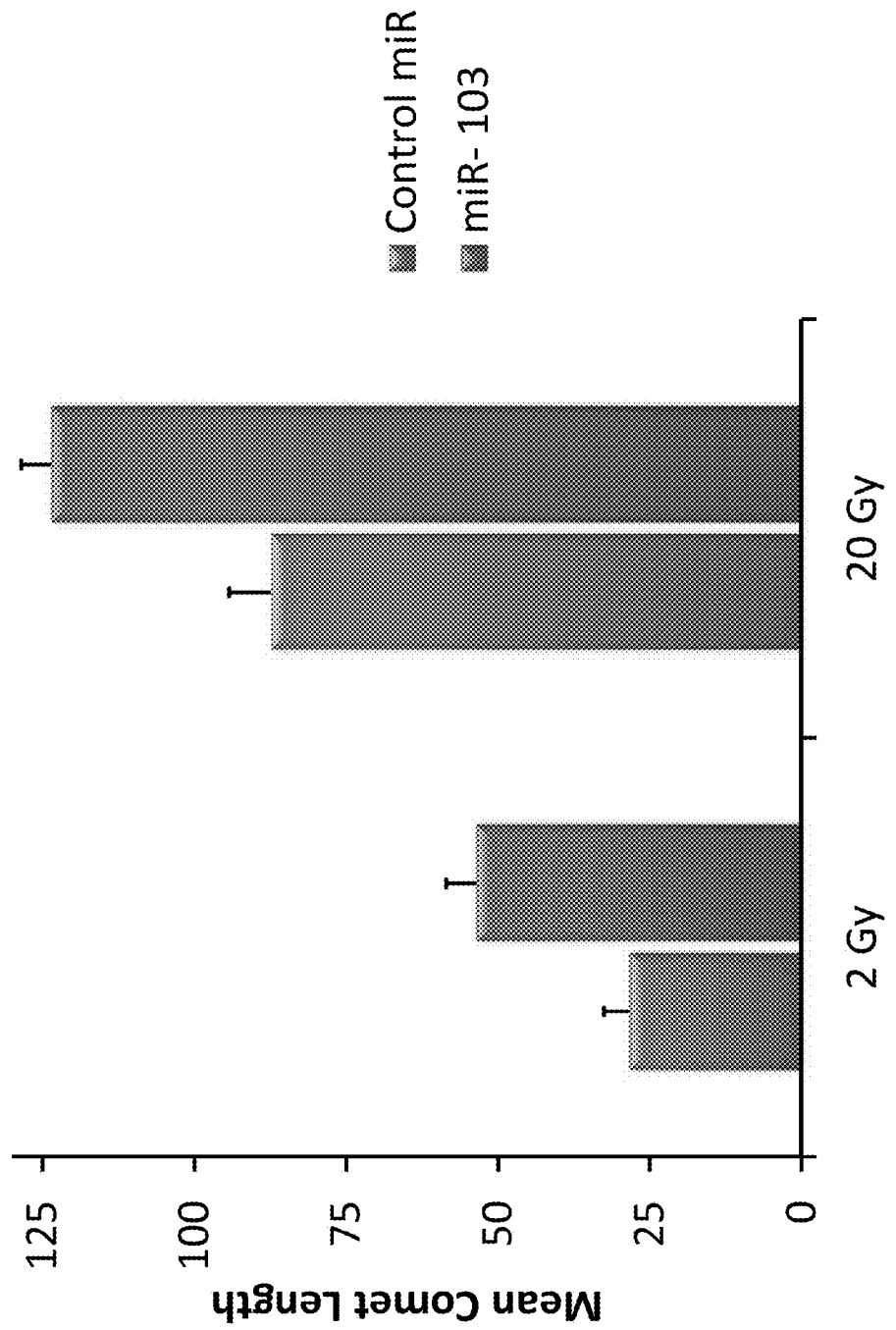
FIG. 13 graphically illustrates data showing that ectopic expression of miR-103 exacerbates endothelial DNA breaks upon irradiation. The data was generated using a DNA damage assay where single cells are electrophoresed on a gel. DNA with double strand breaks trail the nuclei resembling a comet tail. The length of this tail is directly proportional to the amount of DNA double strand breaks. Endothelial cells were transfected as described above, and irradiated (2 and 20 Gy) 24 hours later; and one hour later they were electrophoresed, stained for DNA, imaged and the comet length was measured from fluorescent microscopy images. Conclusion: Expression of miR-103 increases DNA double strand breaks. Together with the previous two slides, this data establishes that the expression of miR-103 leads to increased cell death via DNA damage.
Figure 14:
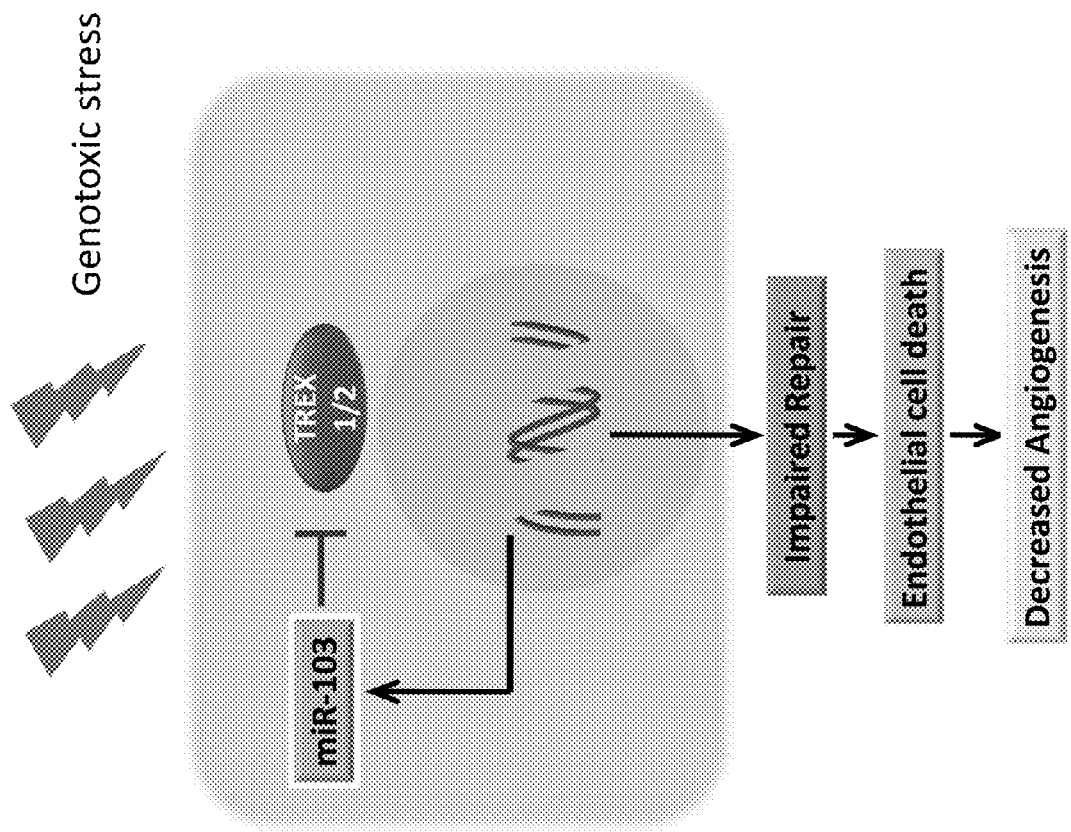
FIG. 14 schematically illustrates that: expression of miR-103 decreases TREX1 protein levels (see also FIG. 8); and, miR-103 mediated loss of DNA repair in response to genotoxic stress facilitates impaired DNA repair, endothelial cell death and decreased angiogenesis.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, the invention provides compositions and methods comprising use of microRNAs and microRNA inhibitors to modulate, including inhibiting or stimulating or modifying, blood vessel growth (angiogenesis, vascularization, or neovascularization), cell and tumor microenvironment patterning, cancer cell and tumor growth and malignant disease (metastasis).

In alternative embodiments, the invention provides compositions and methods for enhancing, modulating or ameliorating physical or chemical effects, e.g., stressors, on endothelial cells, including for example: stressors encountered during disease or physical, radioactive or chemical trauma; genotoxic stress (such as radiation, or chemicals or drugs such as cisplatin); oxidative stress (such as hypoxia, free radicals, including reactive oxygen species); metabolic stress (including nutrient deprivation); and, inflammatory stress (from e.g., cytokines or chemokines and the like such as tumor necrosis factor (TNF) and interferon gamma (INF-gamma). For example, in alternative embodiments, when administering compositions comprising microRNA-103 (miRNA-103, or miR103) or equivalents thereof, including chemically modified and stabilized forms of miR103, in conjunction with standard genotoxic chemotherapies, cancer cell chemotherapies or treatments, or radiation and the like or equivalents, enhanced killing of endothelial cells and decreased angiogenesis, pathologic angiogenesis, or tumor angiogenesis is achieved. In alternative embodiments, by administering anti-microRNA (anti-miRNA-103, or anti-miR103) directed against a microRNA-103 or equivalents thereof, including chemically modified and stabilized forms of anti-miR103, new blood vessel growth, neovascularization or angiogenesis can be started and/or increased, e.g., thus ameliorating physical or chemical effects of stressors.

In alternative embodiments, the invention provides compositions and methods comprising use of microRNA-103 (miRNA-103) to block, slow or reverse the development of new blood vessels, or cancer or tumor cells. While the invention is not limited by any particular mechanism of action, with or without blocking or slowing the development of new blood vessels, using microRNA-103 (miRNA-103), in alternative embodiments, the invention provides compositions and methods to ameliorate, treat, slow to reverse the progress of, cause a regression of or prevent: a macular degeneration, a diabetic retinopathy, a cancer, an inflammatory disease, a psoriasis, a fibrosis, a leprosy, a multiple sclerosis, a disease with an inflammatory component, an inflammatory bowel disease, an ulcerative colitis or a Crohn's disease.

In alternative embodiments, the invention provides compositions and methods comprising use of microRNA-103 (miRNA-103), in conjunction with standard genotoxic chemotherapies or radiation and the like, to achieve enhanced killing of endothelial cells and decrease tumor angiogenesis.

In alternative embodiments, the invention provides compositions and methods comprising use of anti-miRNA-103 (anti-microRNA-103) to augment the growth of blood vessels or cancer or tumor cells. While the invention is not limited by any particular mechanism of action, with or without blocking or slowing the development of new blood vessels, using anti-microRNA-103 (anti-miRNA-103), in alternative embodiments, the invention provides compositions and methods to ameliorate, treat, slow or reverse the progress of, cause a regression of or prevent: a cardiovascular, a thrombotic or an ischemic disease; a stroke; a myocardial infarction; an ischemic disorder associated with a diabetes.

In alternative embodiments, the invention provides compositions and methods comprising use of anti-microRNA-103 (anti-miRNA-103) to protect normal blood vessels during chemotherapy or radiation therapies and the like.

The inventors used a differential screen of treated versus (vs.) untreated Human Umbilical Vein Endothelial Cells (HUVEC) cells to identify which miRNAs respond to a potent genotoxic stress of 20 Gy irradiation (the "gray", symbol: Gy, is the SI unit of absorbed radiation dose of ionizing radiation). They found the most elevated was miRNA-103. They demonstrated miR-103 was also consistently upregulated during other modes of genotoxic stresses including treatment with Cisplatin, Doxirubicin and hydrogen peroxide.

Figure 15:
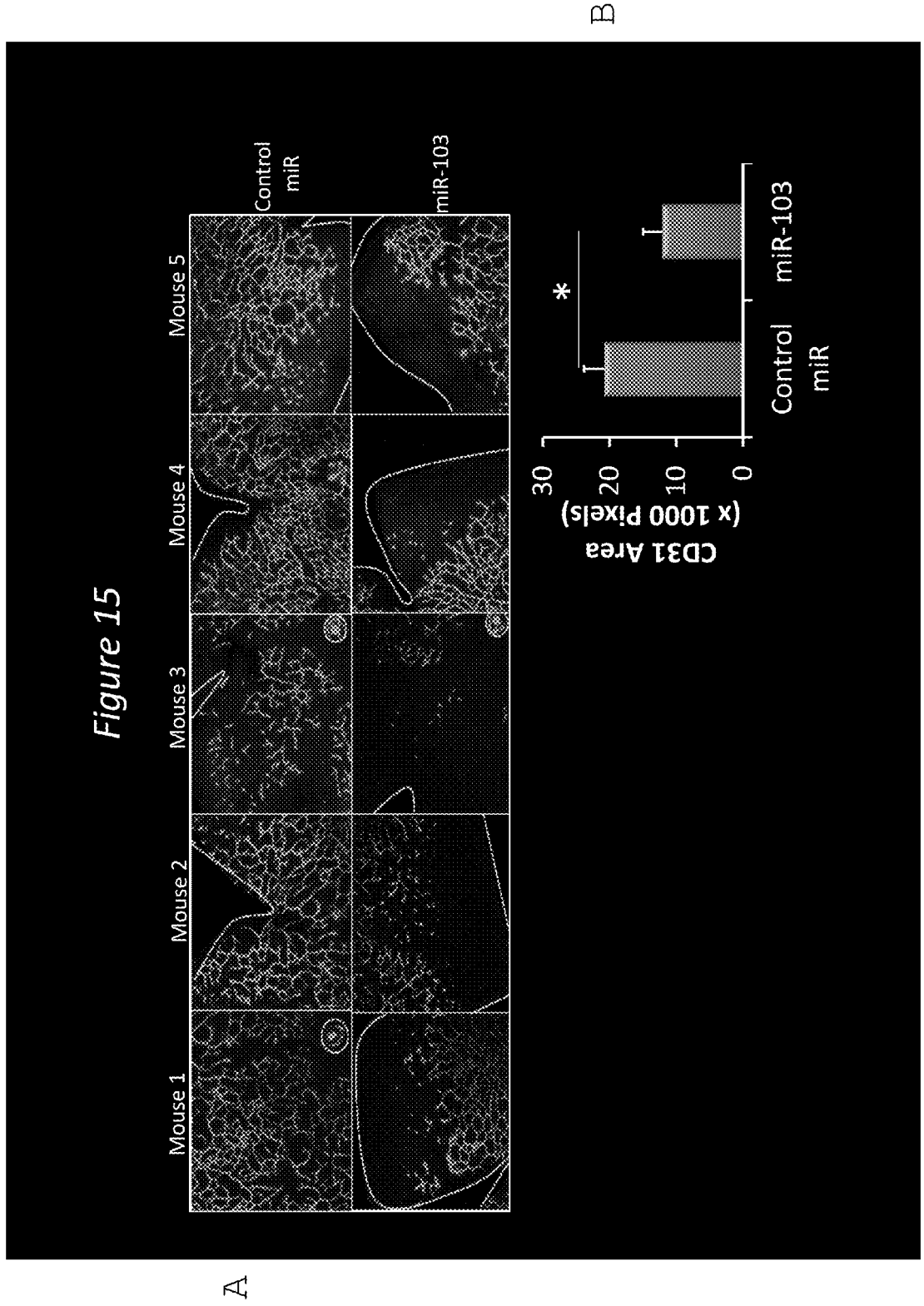
FIG. 15 illustrates data showing that ectopic expression of miR-103 decreases developmental angiogenesis in mouse retina, demonstrating that injection of miR-103 in the eye can decrease angiogenesis in vivo. In brief, neonatal six day old mice (five mice) were injected intraocularly with either a control miR or miR-103; and five days later, the mice were euthanized, retinas were harvested and stained for blood vessels using CD31 antibody.
Figure 16:
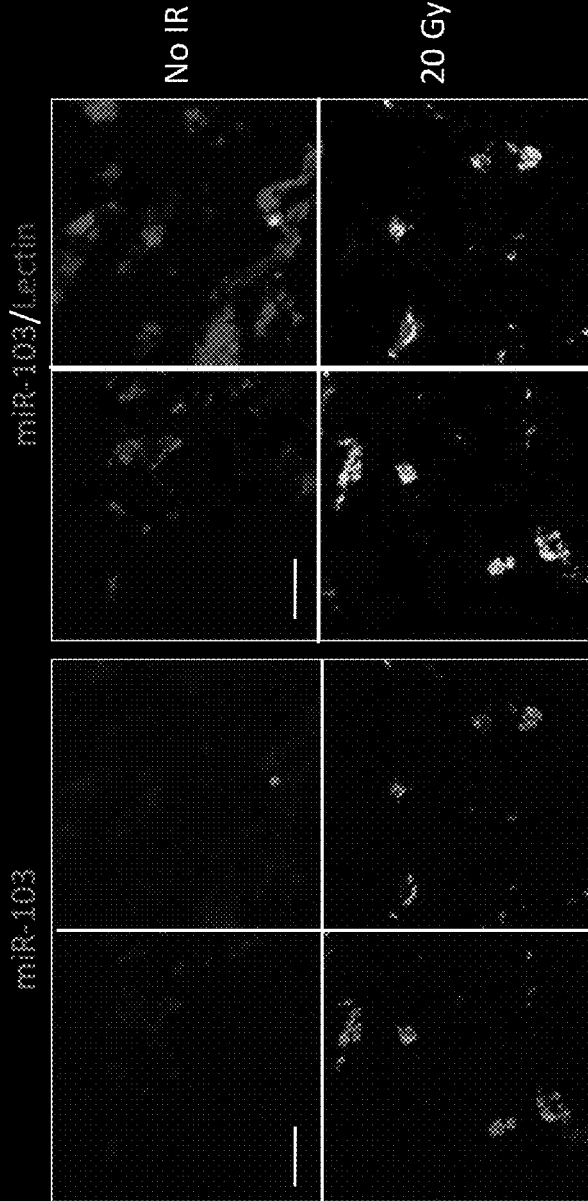
FIG. 16 illustrates data showing that miR-103 is selectively upregulated in tumor endothelial cells upon DNA damage, also showing that high dose irradiation (20 Gy) of a human glioblastoma tumor implanted in mouse brains leads to selective upregulation of miR-103 in endothelial cells (lectin staining) but not tumor cells; this demonstrates that: (1) restoring miR-103 expression in tumor cells can sensitize them to radiation/DNA damage, and (2) delivering a miR-103 of the invention to endothelial cells can mimic the effects of high dose radiation.
Figure 17:
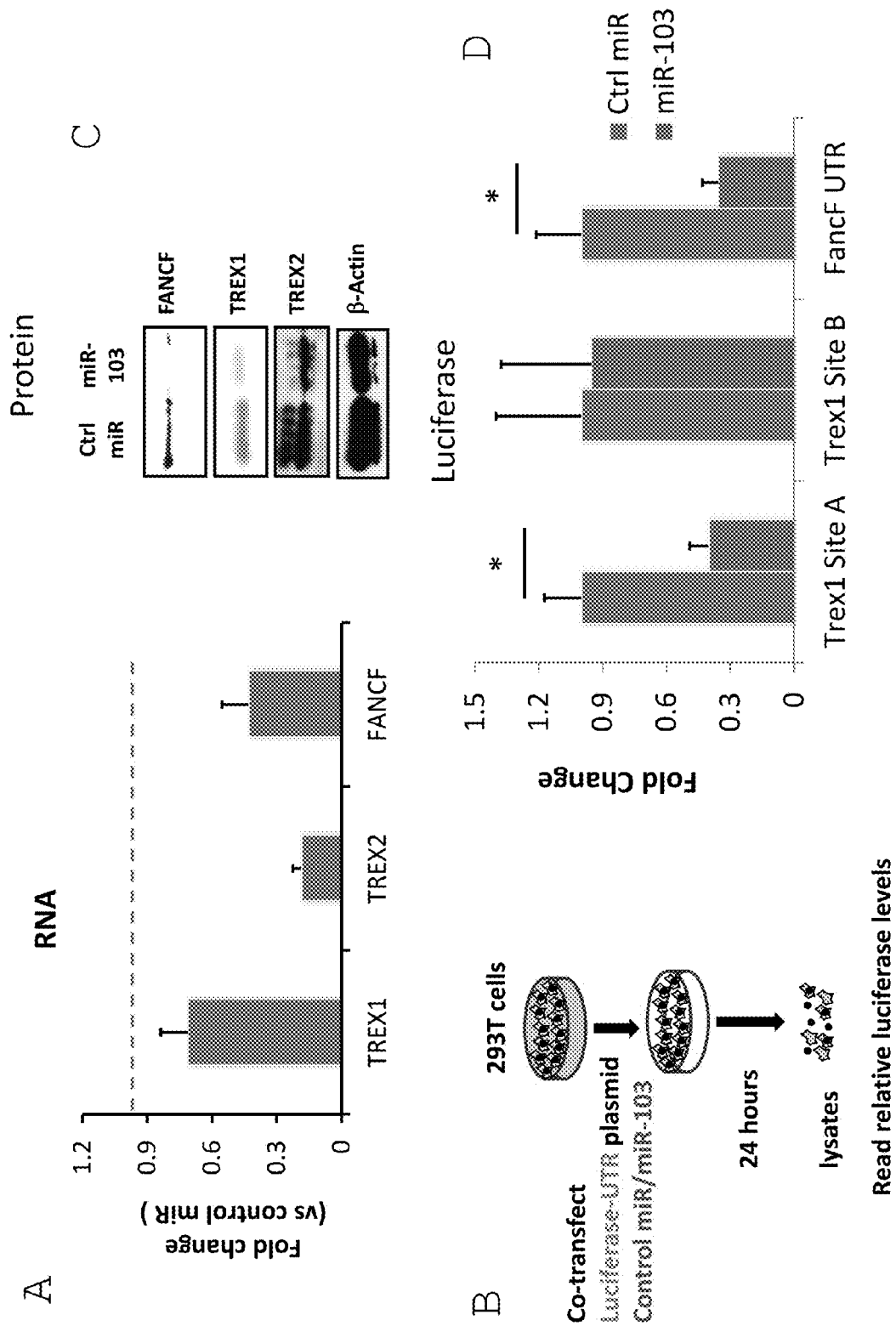
FIG. 17 illustrates data demonstrating that R-103 downregulates FANCF and TREX1 expression in endothelial cells. As schematically illustrated in FIG. 17B, different miR binding sites from the target genes were cloned downstream of a luciferase reporter; then this construct was expressed in cells together with mIR-103 and luciferase levels were assayed 48 hours later.
Figure 18:
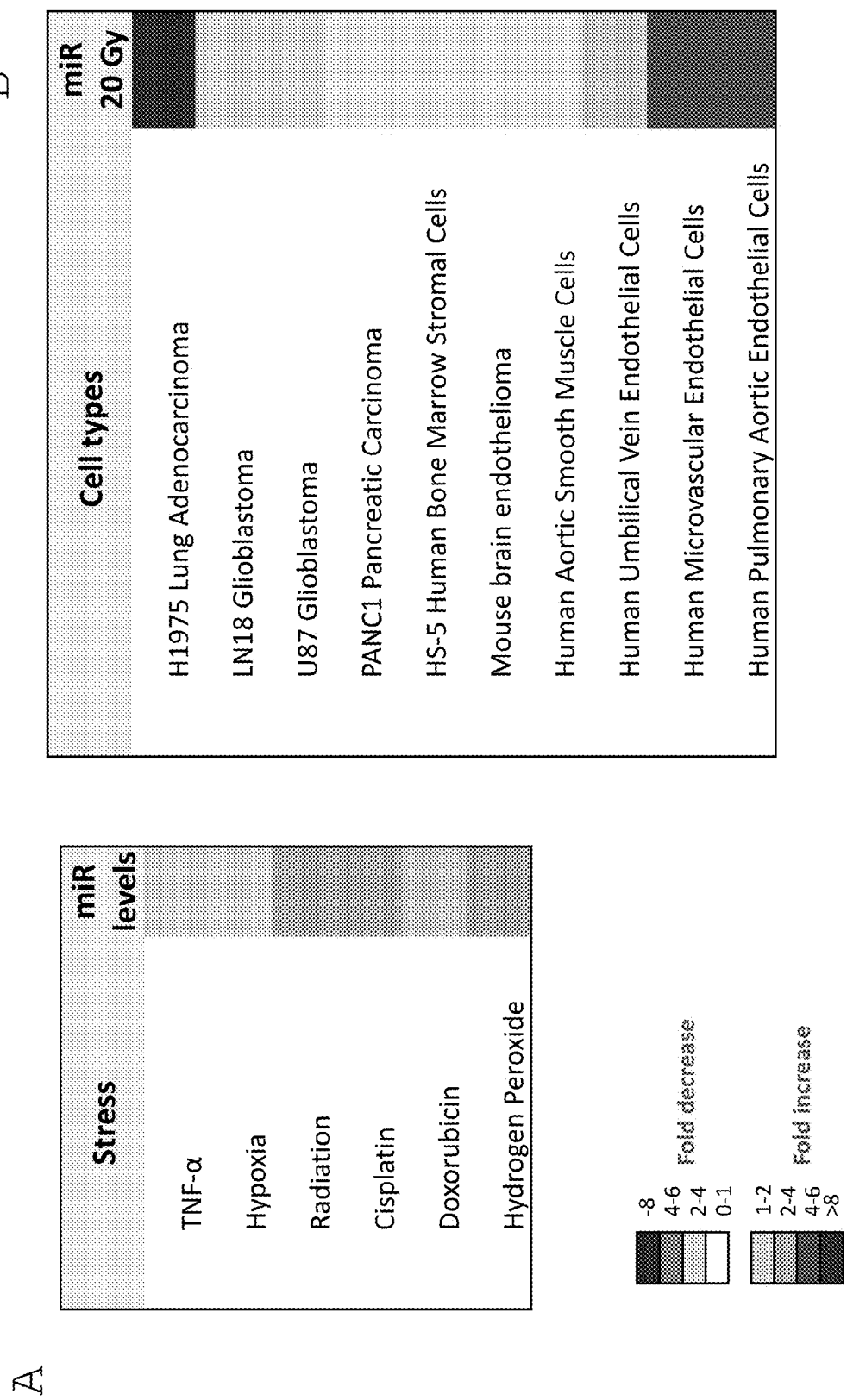
FIG. 18 illustrates data showing that miR-103 is upregulated in response to diverse genotoxic stress stimuli in multiple vascular cell types.
Figure 19:
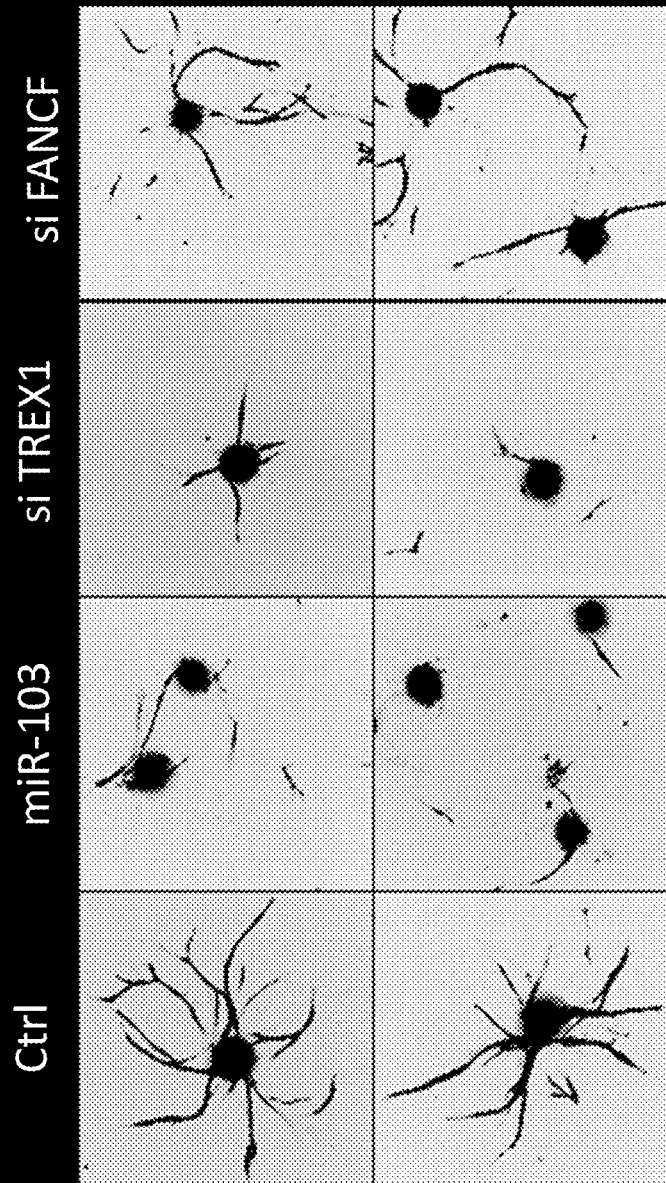
FIG. 19 illustrates data showing that loss of TREX1 or FANCF decreases endothelial tube formation. Endothelial cells were transfected with the indicated reagents and assayed for their ability to undergo sprouting angiogenesis in the bead assay as described earlier. Conclusion: Expression of miR-103 or loss of TREX1/FANCF decreases angiogenesis.
Figure 20:
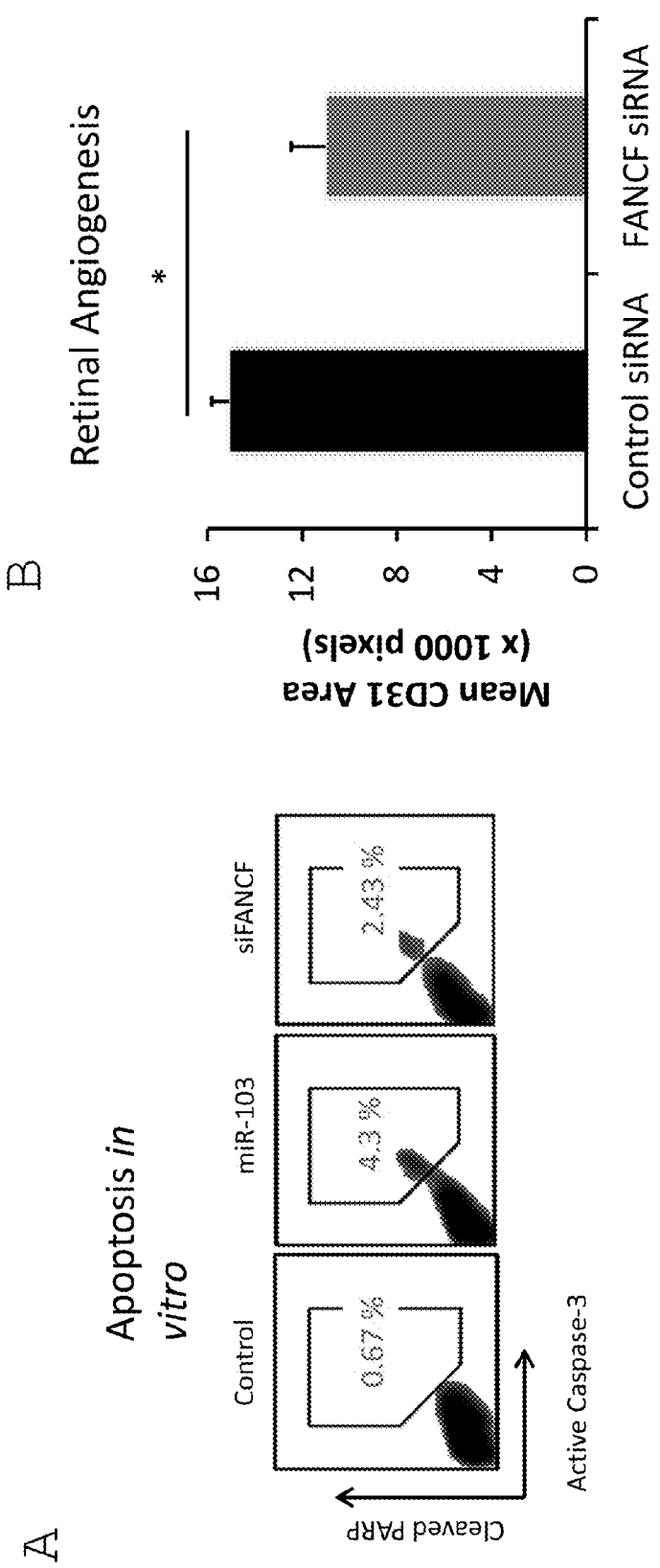
FIG. 20 illustrates data showing loss of FANCF phenocopies miR-103 in vitro and in vivo.
Figure 21:
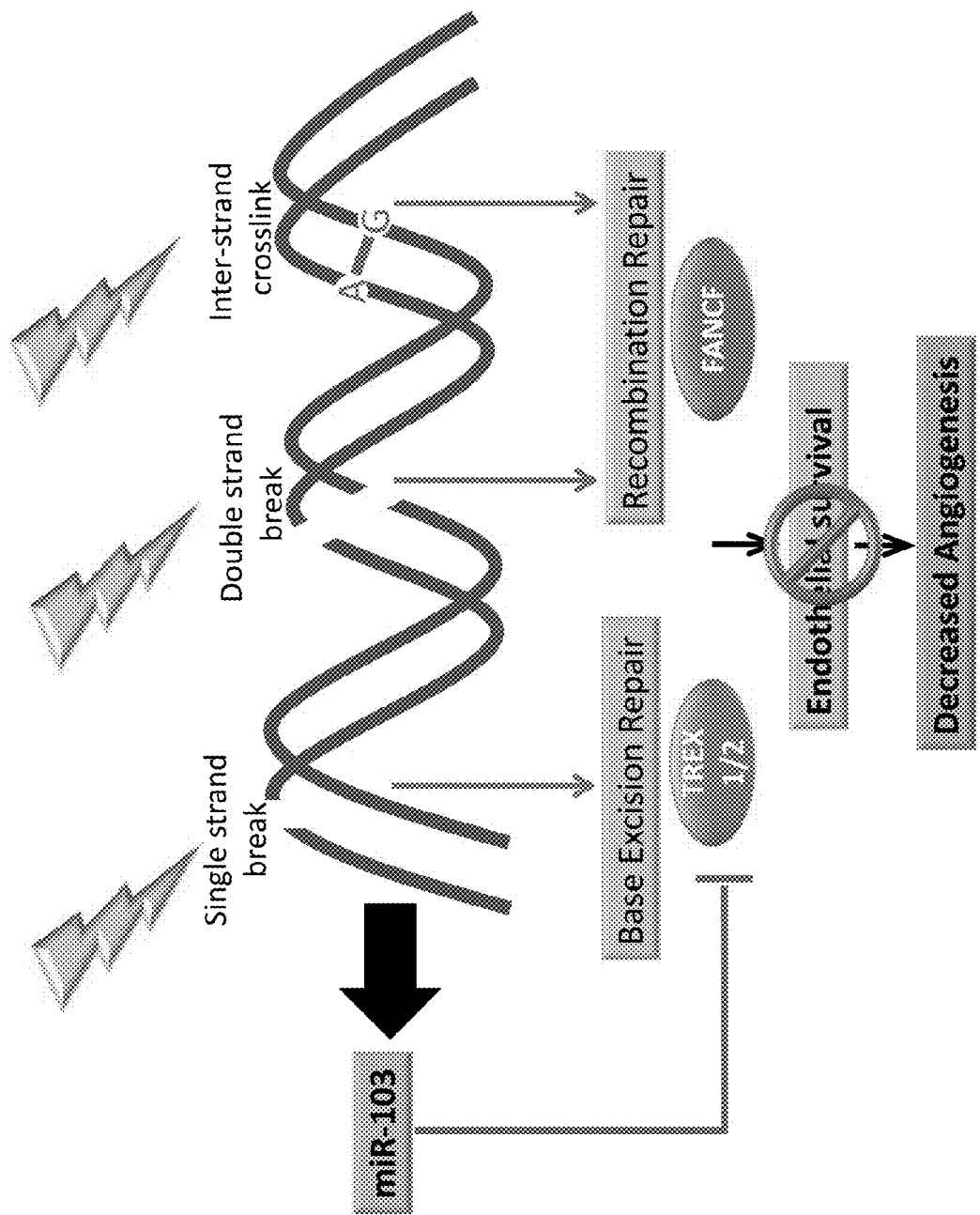
FIG. 21 schematically illustrates how miR-103 downregulates TREX1/2 and FANCF to disrupt endothelial DNA repair and decreases angiogenesis.

They then demonstrated that miRNA-103 decreased tube formation in response to radiation and that anti-miRNA-103 rescued the tube formation. In addition, mRNA profiling identified three downstream targets (FANC, TREX1 and TREX2) that were down-regulated by both genotoxic stress and by miRNA-103. FIG. 15 presents a schematic that shows TREX1/2 enabling repair of DNA damage in response to radiation ("genotoxic stress) with miRNA-103 acting to block the effects of TREX1/2. So, in sum, the compositions and methods of the invention use miRNA-103 to effectively block (or slow, reverse or inhibit) DNA repair, which leads to endothelial cell death and, therefore, decreased angiogenesis.

In alternative embodiments, the invention provides compositions and methods comprising use of miR-103 to slow, reverse, decrease, inhibit or prevent angiogenesis in vivo, in situ or in vitro. In alternative embodiments, the invention provides compositions and methods comprise use of anti-miR-103 to stimulate or promote angiogenesis in vivo, in situ or in vitro.

While the invention is not limited by any particular mechanism of action, in one embodiment, a mechanism of action is by modulating DNA damage responses.

This invention is the first description and demonstration that miR-103 is upregulated in endothelial cells in response to different stress stimuli and mediates the death of endothelial cells in response to irradiation.

Based on mRNA profiling of DNA damage response proteins, we have identified that miR-103 functions by inhibiting DNA repair enzymes TREX1 and TREX2. These proteins are critical for the damage control responses in cells exposed to a variety of genotoxic stresses such as radiation or oxidative damage. Loss of these proteins by increasing the levels of miR-103 in the cells will destabilize the DNA repair responses of cells and force them to undergo cell cycle arrest or cell death. See data described in the Figures. Blocking angiogenesis with mir-103 and reduces the level of disease having a pathogenesis associated with blood vessel growth (including unwanted blood vessel growth), such as retinal age related macular degeneration, diabetic retinopathy, cancer and inflammatory diseases such as rheumatoid arthritis, psoriasis, fibrosis.

In alternative embodiments, the invention provides compositions and methods comprising use of anti-mir-103 for promoting or stimulating or accelerating angiogenesis and/or to resolve, slow the progress of or ameliorate a cardiovascular disease, thrombotic disease, ischemic disease including stroke, myocardial infarction and ischemic disorders associated with diabetes.

High dose radiation and other genotoxic agents up-regulate the expression of miR-103 in endothelial cells; and miR-103 down-regulates critical DNA damage repair pathway proteins leading to increased DNA damage and cell death. Expression of miR-103 leads to endothelial cell death and decreased angiogenesis in vitro and in retinas, as demonstrated in mouse retinas. Thus, while the invention is not limited by any particular mechanism of action, in alternative embodiments the invention provides compositions and methods comprising or using miR-103 in conjunction with standard genotoxic chemotherapies or radiation to achieve enhanced killing of cells, e.g., endothelial cells, to decrease tumor angiogenesis (the miR-103 can be administered before, during and/or after the chemotherapy and/or radiation). Thus, in alternative embodiments compositions and methods of the invention comprising use of miR-103 to radiosensitize or chemosensitize cells, e.g., tumor blood vessel cells or endothelial cells. For example, miR-103 reagents of the invention can be used as an anti-angiogenic agent to sensitize tumor vessels to radiation and other chemotherapies that cause DNA damage. Additionally, in other embodiments, miR-103 reagents of the invention can be used as an anti-angiogenic agent in eye diseases.

Alternatively, in other embodiments, the invention provides compositions and methods using anti-miR-103 and protect normal blood vessels against genotoxic stress during chemotherapy or radiation therapies. The anti-miR-103 can be administered before, during and/or after the chemotherapy and/or radiation.

Pharmaceutical Compositions

In alternative embodiments, the invention provides compositions and methods for inhibiting, blocking, slowing the rate of, or preventing the development of endothelial cells, new blood vessels (angiogenesis), abnormal cells, inflammatory cells, or tumor cells by introducing in vivo microRNA-103 (or equivalents thereof, including chemically modified and stabilized forms of microRNA-103), and thus, in alternative embodiments, the invention provides compositions and methods for reducing, treating or ameliorating the level of disease in a retinal age-related macular degeneration, a diabetic retinopathy, a cancer, a glioblastoma, a neuroma, a neuroblastoma, a colon carcinoma, a hemangioma, an infection; a condition with at least one inflammatory component; an infectious or an inflammatory disease; a rheumatoid arthritis; a psoriasis; a fibrosis; and/or leprosy.

TABLE 1

Diseases characterized or caused by abnormal or excessive angiogenesis

| Organ | Diseases in mice or humans |
|---|---|
| Numerous organs | Cancer (activation of oncogenes; loss of tumor suppressors); infectious diseases (pathogens express angiogenic genes[112], induce angiogenic programs[113] or transform ECs[114]); autoimmume disorders (activation of mast cells and other leukocytes) |
| Blood vessels | Vascular malformations (Tie-2 mutation[68]); DiGeorge syndrome (low VEGF and neuropilin-1 expression[33]); HHT (mutations of endoglin or ALK-1 (ref, 69)); cavernous hemangioma (loss of Cx37 and Cx40 (ref.[44])); atherosclerosis; transplant arteriopathy |
| Adipose tissue | Obesity (angiogenesis induced by fatty diet; weight loss by angiogenesis inhibitors[116]) |
| Skin | Psoriasis, warts, allergic dermatitis, scar keloids, pyogenic granulomas, blistering disease, Kaposi sarcoma in AIDS patients[114] |
| Eye | Persistent hyperplastic vitreous syndrome (loss of Ang-2 (refs, 65,116) or VEGF164 (ref. 18)); diabetic retinopathy; retinopathy of prematurity; choroidal neovascularization (TIMP-3 mutation[51]) |
| Lung | Primary pulmonary hypertension (germline BMPR-2 mutation; somatic EC mutations[73,75,76]); asthma; nasal polyps |
| Intestines | Inflammatory bowel and periodontal disease, ascites, peritoneal adhesions |
| Reproductive system | Endometriosis, uterine bleeding, ovarian cysts, ovarian hyperstimulation[25] |
| Bone, joints | Arthritis, synovitis, osteomyelitis, osteophyte formation[12] |

In alternative embodiments, the invention provides compositions and methods for inhibiting, blocking, slowing the rate of, or preventing the development of endothelial cells, new blood vessels (angiogenesis), abnormal cells, inflammatory cells, or tumor cells, and by introducing in vivo microRNA-103 (or equivalents thereof, including chemically modified and stabilized forms of microRNA-103), and thus, in alternative embodiments, the invention provides compositions and methods for reducing, treating or ameliorating any condition, disease, symptom (for example, as caused by a trauma, exposure to a toxic agent or a radiation, or an infection) or infection characterized or caused by abnormal or excessive or ectopic angiogenesis, including for example, cancer, infectious disease, autoimmune disorders, vascular malformations, DiGeorge syndrome or any condition having low VEGF and/or neuropilin-1 expression, hereditary hemorrhagic telangiectasia (HHT, also known as Osler-Weber-Rendu disease and Osler-Weber-Rendu syndrome), cavernous hemangioma, atherosclerosis, transplant arteriopathy, obesity, angiogenesis caused by a fatty diet, psoriasis, warts, allergic dermatitis, scar keloids, pyogenic granulomas, blistering disease, Kaposi sarcoma (e.g., in AIDS patients), persistent hyperplastic vitreous syndrome, a retinopathy, diabetic retinopathy, retinopathy of prematurity, choroidal neovascularization, primary pulmonary hypertension, asthma, nasal polyps, inflammatory bowel disease, periodontal disease, ascites, peritoneal adhesions, endometriosis, uterine bleeding, a cyst, an ovarian cyst, an ovarian hyperstimulation, tendonitis, arthritis, synovitis, osteomyelitis or osteophyte formation; or, any disease, trauma or condition listed in Table 1.

In alternative embodiments, the invention provides compositions and methods to stimulate or augment the growth of blood vessels or tumor cells by introducing in vivo an anti-microRNA-103 (or equivalents thereof, including chemically modified and stabilized forms of anti-miR103), and thus, in alternative embodiments, anti-miR-103 is used to protect normal blood vessels against genotoxic stress during chemotherapy or radiation therapies.

In alternative embodiments, the invention provides compositions and methods to stimulate, accelerate or augment the growth of blood vessels or tumor cells by introducing in vivo an anti-microRNA-103 (or equivalents thereof, including chemically modified and stabilized forms of anti-miR103), and thus, in alternative embodiments, the invention provides compositions and methods for reducing, treating or ameliorating any condition, disease, symptom (for example, as caused by a trauma, exposure to a toxic agent or a radiation, or an infection) or infection characterized or caused by lack of appropriate vascularization or under-vascularization, and in alternative embodiments, the invention provides compositions and methods for reducing, treating or ameliorating any disease, trauma or condition caused or exacerbated by vasoconstriction; microvascular degeneration and/or cerebral angiopathy caused by e.g., trauma or amyloid beta toxicity; Alzheimer's disease; amyotropic lateral sclerosis or diabetic neuropathy; any disease, trauma or condition caused or exacerbated by impaired perfusion and/or neuroprotection, e.g., causing motoneuron or axon degeneration, e.g., due to VEGF production; stroke; arteriopathy; atherosclerosis; any disease, trauma or condition caused or exacerbated by impaired collateral vessel development; hypertension; any disease, trauma or condition caused or exacerbated by microvessel rarefaction, e.g., due to impaired vasodilation or angiogenesis; diabetes; any disease, trauma or condition caused or exacerbated by impaired collateral growth and/or angiogenesis in ischemic limbs; restenosis; any disease, trauma or condition caused or exacerbated by impaired re-endothelialization, e.g., after arterial injury, e.g., in old age; gastric or oral ulcerations; any disease, trauma or condition caused or exacerbated by delayed healing, e.g., due to production of angiogenesis inhibitors by e.g., toxins or pathogens; Crohn's disease; any disease, trauma or condition caused or exacerbated by mucosal ischemia; hair loss; any disease, trauma or condition caused or exacerbated by retarded or impaired hair growth, e.g., by angiogenesis inhibitors or toxins; skin purpura; telangiectasia; venous lake formation; any disease, trauma or condition caused or exacerbated by reduction of vessel number and/or maturation, e.g., which can be age-dependent, e.g., due to telomere shortening; pre-eclampsia; any disease, trauma or condition caused or exacerbated by endothelial cell dysfunction, e.g., resulting in an organ failure, thrombosis and/or a hypertension, e.g., due to deprivation of e.g., VEGF or another cytokine; menorrhagia or uterine bleeding; any disease, trauma or condition caused or exacerbated by fragility of blood vessels, e.g., due to low Ang-1 production; neonatal respiratory distress; any disease, trauma or condition caused or exacerbated by insufficient lung maturation and/or surfactant production e.g., in premature individuals, e.g., due to reduced VEGF production; pulmonary fibrosis; emphysema; any disease, trauma or condition caused or exacerbated by alveolar apoptosis, e.g., upon VEGF inhibition, or caused by a toxin; nephropathy; any disease, trauma or condition caused or exacerbated by nephron-vessel loss, e.g., which can be age-related; osteoporosis; impaired bone fracture healing; any disease, trauma or condition caused or exacerbated by impaired bone formation, e.g., due to age, or age-related or age-dependent decline of VEGF-driven angiogenesis; any disease, trauma or condition caused or exacerbated by inhibition of fracture healing; or, any disease, trauma or condition listed in Table 2.

TABLE 2

Diseases characterized or caused by insufficient angiogenesis or vessel regression

| Organ | Disease in mice or humans | Angiogenic mechanism |
| --- | --- | --- |
| Nervous system | Alzheimer disease | Vasoconstriction, microvascular degeneration and cerebral angiopathy due to EC toxicity by amyloid-$\beta$[117] |
| | Amyotrophic lateral sclerosis, diabetic neuropathy | Impaired perfusion and neuroprotection, causing motoneuron or axon degeneration due to insufficient VEGF production[39] |
| | Stroke | Correlation of survival with angiogenesis in brain[118]; stroke due to arteriopathy (Notch-3 mutations[20]) |

TABLE 2-continued

Diseases characterized or caused by insufficient angiogenesis or vessel regression

| Organ | Disease in mice or humans | Angiogenic mechanism |
| --- | --- | --- |
| Blood vessels | Atherosclerosis | Characterized by impaired collateral vessel development[119] |
| | Hypertension | Microvessel rarefaction due to impaired vaasodilation or angiogenesis[105] |
| | Diabetes | Characterized by impaired collateral growth[120] and angiogenesis in ischemic limbs[121], but enhanced retinal neovascularization secondary to pericyte dropout |
| | Restenosis | Impaired re-endothelialization after arterial injury at old age[122] |
| Gastrointestinal | Gastric or oral ulcerations | Delayed healing due to production of angiogenesis inhibitors by pathogens[123]. |
| | Crohn disease | Characterized by mucosal ischemia |
| Skin | Hair loss | Retarded hair growth by angiogenesis inhibitors[124] |
| | Skin purpura, telanglectasia and venous take formation | Age-dependent reduction of vessel number and maturation (SMC dropout) due to EC talomers shortening[125] |
| Reproductive system | Pre-eciampsia | EC dysfunction resulting in organ failure, thrombosis and hypertension due to deprivation of VEGF by soluble Flt-1 (ref. 126) |
| | Menonhagia (uterine bleeding) | Fragility of SMC-poor vessels duto to low Ang-1 production[127] |
| Lung | Neonatal respiratioy distress | insufficient lung maturation and surfactant production in premature mice due to reduced HIF-2α and VEGF production[126] |
| | Pulmonary fibrosis, emphysema | Alveolar EC apoptosis upon VEGF inhibition[129] |
| Kidney | Nephropathy | Age-related vessel loss due to TSP-1 production[130] |
| Bone | Osteoporosis, impaired bone fracture healing | Impaired bone fomation due to age dependent decline of VEGF-driven angiogenesis[131], angiogenesis inhibitors prevent fracture healing[132] |

In alternative embodiments, the invention provides pharmaceutical compositions for practicing the methods of the invention, e.g., pharmaceutical compositions for ameliorating, preventing and/or treating diseases, infections and/or conditions having unwanted, pathological or aberrant blood vessel growth (angiogenesis) or cell proliferation, or that are responsive to inhibition or arrest of cell growth due to inhibition of new blood vessel growth (angiogenesis), by in vivo administration of microRNA-103. The invention provides compositions as described herein, including pharmaceutical compositions, e.g., in the manufacture of medicaments for ameliorating, preventing and/or treating diseases, infections and/or conditions having unwanted, pathological or aberrant cell proliferation or blood vessel growth.

In alternative embodiments, compositions used to practice the invention (e.g., microRNA-103 or anti-microRNA-103) are formulated with a pharmaceutically acceptable carrier. In alternative embodiments, the pharmaceutical compositions used to practice the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

For designing microRNA-103 or anti-microRNA-103, the mature sequence of miR-103 (5'-AGCAGCAUUGUA-CAGGGCUAUGA-3') SEQ ID NO:1) can be retrieved from an miRBase Sequence Database, e.g., the miRBase of the Univ. of Manchester, Great Britain. *Homo sapiens* microRNA 103b-1 (MIR103B1), microRNA is: TCATAGC-CCT GTACAATGCT GCTTGATCCA TATGCAACAA GGCAGCACTG TAAAGAAGCC GA (SEQ ID NO:2): see e.g., Azuma-Mukai, A., et al., Proc. Natl. Acad. Sci. U.S.A. 105 (23):7964-7969 (2008).

While the invention is not limited by any particular mechanism of action: microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA.

In alternative embodiments pharmaceutical compositions used to practice the invention are administered in the form of a dosage unit, e.g., a tablet, capsule, bolus, spray. In alternative embodiments, pharmaceutical compositions comprise a microRNA (e.g., an miRNA-103 or anti-miRNA-103) in a dose: e.g., 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, or 850 mg or more.

In alternative embodiments, a microRNA (e.g., an miRNA-103 or anti-miRNA-103) of the invention is administered as a pharmaceutical agent, e.g., a sterile formulation, e.g., a lyophilized microRNA that is reconstituted with a suitable diluent, e.g., sterile water for injection or sterile saline for injection. In alternative embodiments the reconstituted product is administered as a subcutaneous injection or as an intravenous infusion after dilution into saline. In alternative embodiments the lyophilized drug product comprises microRNA prepared in water for injection, or in saline for injection, adjusted to about pH 7.0 to 9.0 with acid or base during preparation, and then lyophilized. In alternative embodiments a lyophilized microRNA of the invention (e.g., an miRNA-103 or anti-miRNA-103) is between about 25 to 800 or more mg, or about 10, 15, 20, 25, 30, 35, 40, 45, 50, 75, 100, 125, 150, 175, 200, 225, 250, 275, 300, 325, 350, 375, 425, 450, 475, 500, 525, 550, 575, 600, 625, 650, 675, 700, 725, 750, 775, 800 or 850 mg or more of a microRNA of the invention. The lyophilized microRNA of the invention can be packaged in a 2 mL Type I, clear glass vial (e.g., ammonium sulfate-treated), e.g., stoppered with a bromobutyl rubber closure and sealed with an aluminum overseal.

Combination Formulations and Treatments

In alternative embodiments, the invention provides compositions and methods comprising use of both a microRNA (e.g., an miRNA-103 or anti-miRNA-103, or equivalents thereof, including chemically modified and stabilized forms thereof) of the invention, and at least one additional composition, drug, nutrient, or treatment. The additional composition, drug, nutrient, or treatment can be another microRNA, an siRNA, a nucleic acid, an inhibitory nucleic acid such as an antisense DNA or RNA, a lipid, a polysaccharide, a protein or a peptide, a small molecule, a drug, a nanoparticle, a radioisotope or radionuclide, and the like. In alternative embodiments, the additional composition, drug, nutrient, or treatment can be administered before, with or after administration of a microRNA used to practice this invention, or can be co-formulated with a microRNA used to practice this invention.

For example, in alternative embodiments, when administering compositions of the invention that induce apoptosis or cell death, or when practicing methods of the invention that induce apoptosis or cell death (e.g., expression of or administration of miR-103), the at least one additional composition, drug, nutrient, or treatment that can cause or increase the amount of DNA damage and/or inhibit a poly(ADP-ribose) polymerase (PARP), for example, practicing the invention can further comprise use of or administration of: an inhibitor of poly(ADP-ribose) polymerase (PARP) such as: an iniparib, an olaparib, a veliparib, a rucaparib or a 3-aminobenzamide; and/or a DNA damaging agent such as: a cisplatin (e.g., PLATIN™), a carboplatin (e.g., PARAPLATIN™), an oxaliplatin (e.g., ELOXATIN™), an etoposide (e.g., ETOPOPHOS™) or a doxorubicin (e.g., DOXIL™) or another topoisomerase inhibitor (e.g., teniposide (e.g., VUMON™), doxorubicin, daunorubicin, mitoxantrone, amsacrine, ellipticine, aurintricarboxylic acid, irinotecan, topotecan, camptothecin and lamellarin D), radiation and their derivatives. In alternative embodiments, the drug is, or drugs are, co-formulated with, or is administered with, a composition of the invention, e.g., a microRNA-103 (miRNA-301, or miR301) or equivalents thereof, including chemically modified and stabilized forms of miR301.

microRNA Modifications

In alternative embodiments, the invention provides compositions and methods comprising in vivo delivery of microRNAs (e.g., an miRNA-103 or anti-miRNA-103). In practicing the invention, the microRNAs can be modified, e.g., in alternative embodiments, at least one nucleotide of microRNA construct is modified, e.g., to improve its resistance to nucleases, serum stability, target specificity, blood system circulation, tissue distribution, tissue penetration, cellular uptake, potency, and/or cell-permeability of the polynucleotide. In alternative embodiments, the microRNA construct is unmodified. In other embodiments, at least one nucleotide in the microRNA construct is modified.

In alternative embodiments, guide strand modifications are made to increase nuclease stability, and/or lower interferon induction, without significantly decreasing microRNA activity (or no decrease in microRNA activity at all). In certain embodiments, the modified microRNA constructs have improved stability in serum and/or cerebral spinal fluid compared to an unmodified structure having the same sequence.

In alternative embodiments, a modification includes a 2'-H or 2'-modified ribose sugar at the second nucleotide from the 5'-end of the guide sequence. In alternative embodiments, the guide strand (e.g., at least one of the two single-stranded polynucleotides) comprises a 2'-O-alkyl or 2'-halo group, such as a 2'-O-methyl modified nucleotide, at the second nucleotide on the 5'-end of the guide strand, or, no other modified nucleotides. In alternative embodiments, polynucleotide constructs having such modification may have enhanced target specificity or reduced off-target silencing compared to a similar construct without the 2'-O-methyl modification at the position.

In alternative embodiments, a second nucleotide is a second nucleotide from the 5'-end of the single-stranded polynucleotide. In alternative embodiments, a "2'-modified ribose sugar" comprises ribose sugars that do not have a 2'-OH group. In alternative embodiments, a "2'-modified ribose sugar" does not include 2'-deoxyribose (found in unmodified canonical DNA nucleotides), although one or more DNA nucleotides may be included in the subject constructs (e.g., a single deoxyribonucleotide, or more than one deoxyribonucleotide in a stretch or scattered in several parts of the subject constructs). For example, the 2'-modified ribose sugar may be 2'-O-alkyl nucleotides, 2'-deoxy-2'-fluoro nucleotides, 2'-deoxy nucleotides, or combination thereof.

In alternative embodiments, a microRNA construct of the invention comprises one or more 5'-end modifications, e.g., as described above, and can exhibit a significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the microRNA construct of the invention.

In alternative embodiments, a microRNA construct of the invention comprises a guide strand modification that further increase stability to nucleases, and/or lowers interferon induction, without significantly decreasing microRNA activity (or no decrease in microRNA activity at all). In alternative embodiments, the 5'-stem sequence comprises a 2'-modified ribose sugar, such as 2'-O-methyl modified nucleotide, at the second nucleotide on the 5'-end of the polynucleotide, or, no other modified nucleotides. In alternative embodiments the hairpin structure having such modification has enhanced target specificity or reduced off-target silencing compared to a similar construct without the 2'-O-methyl modification at same position.

In alternative embodiments, the 2'-modified nucleotides are some or all of the pyrimidine nucleotides (e.g., C/U). Examples of 2'-O-alkyl nucleotides include a 2'-O-methyl nucleotide, or a 2'-O-allyl nucleotide. In alternative embodiments, the modification comprises a 2'-O-methyl modification at alternative nucleotides, starting from either the first or the second nucleotide from the 5'-end. In alternative embodiments, the modification comprises a 2'-O-methyl modification of one or more randomly selected pyrimidine nucleotides (C or U). In alternative embodiments, the modification comprises a 2'-O-methyl modification of one or more nucleotides within the loop.

In alternative embodiments, the modified nucleotides are modified on the sugar moiety, the base, and/or the phosphodiester linkage. In alternative embodiments the modification comprise a phosphate analog, or a phosphorothioate linkage; and the phosphorothioate linkage can be limited to one or more nucleotides within the loop, a 5'-overhang, and/or a 3'-overhang.

In alternative embodiments, the phosphorothioate linkage may be limited to one or more nucleotides within the loop, and 1, 2, 3, 4, 5, or 6 more nucleotide(s) of the guide sequence within the double-stranded stem region just 5' to the loop. In alternative embodiments, the total number of nucleotides having the phosphorothioate linkage may be about 12-14. In alternative embodiments, all nucleotides having the phosphorothioate linkage are not contiguous. In alternative embodiments, the modification comprises a 2'-O-methyl modification, or, no more than 4 consecutive nucleotides are modified. In alternative embodiments, all nucleotides in the 3'-end stem region are modified. In alternative embodiments, all nucleotides 3' to the loop are modified.

In alternative embodiments, the 5'- or 3'-stem sequence comprises one or more universal base-pairing nucleotides. In alternative embodiments universal base-pairing nucleotides include extendable nucleotides that can be incorporated into a polynucleotide strand (either by chemical synthesis or by a polymerase), and pair with more than one pairing type of specific canonical nucleotide. In alternative embodiments, the universal nucleotides pair with any specific nucleotide. In alternative embodiments, the universal nucleotides pair with four pairings types of specific nucleotides or analogs thereof. In alternative embodiments, the universal nucleotides pair with three pairings types of specific nucleotides or analogs thereof. In alternative embodiments, the universal nucleotides pair with two pairings types of specific nucleotides or analogs thereof.

In alternative embodiments, a microRNA of the invention comprises a modified nucleoside, e.g., a sugar-modified nucleoside. In alternative embodiments, the sugar-modified nucleosides can further comprise a natural or modified heterocyclic base moiety and/or a natural or modified internucleoside linkage; or can comprise modifications independent from the sugar modification. In alternative embodiments, a sugar modified nucleoside is a 2'-modified nucleoside, wherein the sugar ring is modified at the 2' carbon from natural ribose or 2'-deoxy-ribose.

In alternative embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In alternative embodiments, the bicyclic sugar moiety is an L sugar in the beta configuration.

In alternative embodiments, the bicyclic sugar moiety comprises a bridge group between the 2' and the 4'-carbon atoms. In alternative embodiments, the bridge group comprises from 1 to 8 linked biradical groups. In alternative embodiments, the bicyclic sugar moiety comprises from 1 to 4 linked biradical groups. In alternative embodiments, the bicyclic sugar moiety comprises 2 or 3 linked biradical groups.

In alternative embodiments, the bicyclic sugar moiety comprises 2 linked biradical groups. In alternative embodiments, a linked biradical group is selected from —O—, —S—, —N(R1)-, —C(R1)(R$_2$)—, —C(R1)=C(R1)-, —C(R1)=N—, —C(=NR1)-, —Si(R1)(R$_2$)—, —S(=O)$_2$—, —S(=O)—, —C(=O)— and —C(=S)—; where each R1 and R$_2$ is, independently, H, hydroxyl, C1 to C$_{12}$ alkyl, substituted C1-C12 alkyl, C$_2$-C12 alkenyl, substituted C$_2$-C12 alkenyl, C$_2$-C$_{12}$ alkynyl, substituted C$_2$-C12 alkynyl, C$_2$-C20 aryl, substituted C$_2$-C20 aryl, a heterocycle radical, a substituted heterocycle radical, heteroaryl, substituted heteroaryl, C$_2$-C$_7$ alicyclic radical, substituted C$_2$-C$_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, C1-C$_{12}$ alkyl, substituted C1-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, amino, substituted amino, acyl, substituted acyl, C1-C$_{12}$ aminoalkyl, C1-C$_{12}$ aminoalkoxy, substituted C1-C$_{12}$ aminoalkyl, substituted C1-C$_{12}$ aminoalkoxy or a protecting group.

In alternative embodiments, the bicyclic sugar moiety is bridged between the 2' and 4' carbon atoms with a biradical group selected from —O—(CH$_2$)x-, —O—CH$_2$—, —O—CH$_2$CH$_2$—, —O—CH(alkyl)-, —NH—(CH2)P—, —N(alkyl)-(CH$_2$)x-, —O—CH(alkyl)-, —(CH(alkyl))—(CH$_2$)x-, —NH—O—(CH2)x-, —N(alkyl)-O—(CH$_2$)x-, or —O—N(alkyl)-(CH$_2$)x-, wherein x is 1, 2, 3, 4 or 5 and each alkyl group can be further substituted. In certain embodiments, x is 1, 2 or 3.

In alternative embodiments, a 2'-modified nucleoside comprises a 2'-substituent group selected from halo, allyl, amino, azido, SH, CN, OCN, CF$_3$, OCF$_3$, O—, S—, or N(Rm)-alkyl; O—, S—, or N(Rm)-alkenyl; O—, S— or N(Rm)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(Rm)(Rn) or O—CH2-C(=O)—N(Rm)(Rn), where each Rm and Rn is, independently, H, an amino protecting group or substituted or unsubstituted C1-C10 alkyl. These 2'-substituent groups can be further substituted with one or more substituent groups independently selected from hydroxyl, amino, alkoxy, carboxy, benzyl, phenyl, nitro (NO.sub.2), thiol, thioalkoxy (S-alkyl), halogen, alkyl, aryl, alkenyl and alkynyl.

In alternative embodiments, a 2'-modified nucleoside comprises a 2'-substituent group selected from F, O—CH$_3$, and OCH$_2$CH$_2$OCH$_3$.

In alternative embodiments, a sugar-modified nucleoside is a 4'-thio modified nucleoside. In alternative embodiments, a sugar-modified nucleoside is a 4'-thio-2'-modified nucleoside. In alternative embodiments a 4'-thio modified nucleoside has a .beta.-D-ribonucleoside where the 4'-O replaced with 4'-S. A 4'-thio-2'-modified nucleoside is a 4'-thio modified nucleoside having the 2'-OH replaced with a 2'-substituent group. In alternative embodiments 2'-substituent groups include 2'-OCH3,2'-O—(CH2).sub.2-OCH3, and 2'-F.

In alternative embodiments, a modified oligonucleotide of the present invention comprises one or more internucleoside modifications. In alternative embodiments, each internucleoside linkage of a modified oligonucleotide is a modified internucleoside linkage. In alternative embodiments, a modified internucleoside linkage comprises a phosphorus atom.

In alternative embodiments, a modified microRNA comprises at least one phosphorothioate internucleoside linkage. In certain embodiments, each internucleoside linkage of a modified oligonucleotide is a phosphorothioate internucleoside linkage.

In alternative embodiments, a modified internucleoside linkage does not comprise a phosphorus atom. In alternative embodiments, an internucleoside linkage is formed by a short chain alkyl internucleoside linkage. In alternative embodiments, an internucleoside linkage is formed by a cycloalkyl internucleoside linkages. In alternative embodiments, an internucleoside linkage is formed by a mixed heteroatom and alkyl internucleoside linkage. In alternative embodiments, an internucleoside linkage is formed by a mixed heteroatom and cycloalkyl internucleoside linkages. In alternative embodiments, an internucleoside linkage is formed by one or more short chain heteroatomic internucleoside linkages. In alternative embodiments, an internucleoside linkage is formed by one or more heterocyclic internucleoside linkages. In alternative embodiments, an internucleoside linkage has an amide backbone, or an internucleoside linkage has mixed N, O, S and CH2 component parts.

In alternative embodiments, a modified oligonucleotide comprises one or more modified nucleobases. In certain embodiments, a modified oligonucleotide comprises one or more 5-methylcytosines, or each cytosine of a modified oligonucleotide comprises a 5-methylcytosine.

In alternative embodiments, a modified nucleobase comprises a 5-hydroxymethyl cytosine, 7-deazaguanine or 7-deazaadenine, or a modified nucleobase comprises a 7-deazaadenine, 7-deazaguanosine, 2-aminopyridine or a 2-pyridone, or a modified nucleobase comprises a 5-substituted pyrimidines, 6-azapyrimidines and N-2, N-6 and O-6 substituted purines, or a 2 aminopropyladenine, 5-propynyluracil or a 5-propynylcytosine.

In alternative embodiments, a modified nucleobase comprises a polycyclic heterocycle, or a tricyclic heterocycle; or, a modified nucleobase comprises a phenoxazine derivative, or a phenoxazine further modified to form a nucleobase or G-clamp.

Nanoparticles and Liposomes

The invention also provides nanoparticles and liposomal membranes comprising compounds used to practice the invention, e.g., microRNA-103 or anti-microRNA-103. Thus, in alternative embodiments, the invention provides nanoparticles and liposomal membranes targeting diseased and/or tumor (cancer) stem cells and dysfunctional stem cells, and angiogenic cells.

In alternative embodiments, the invention provides nanoparticles and liposomal membranes comprising (in addition to comprising compounds used to practice the methods of the invention) molecules, that selectively target abnormally growing, diseased, infected, dysfunctional and/or cancer (tumor) cell receptors. In alternative embodiments, the invention provides nanoparticles and liposomal membranes using IL-11 receptor and/or the GRP78 receptor to targeted receptors on cells, e.g., on tumor cells, e.g., on prostate or ovarian cancer cells. See, e.g., U.S. patent application publication no. 20060239968.

In one aspect, the compositions used to practice the invention are specifically targeted for inhibiting, ameliorating and/or preventing endothelial cell migration and for inhibiting angiogenesis, e.g., tumor-associated or disease- or infection-associated neovasculature.

The invention also provides nanocells to allow the sequential delivery of two different therapeutic agents with different modes of action or different pharmacokinetics, at least one of which comprises a composition used to practice the methods of the invention. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., such as a retinal age-related macular degeneration, a diabetic retinopathy, a cancer or carcinoma, a glioblastoma, a neuroma, a neuroblastoma, a colon carcinoma, a hemangioma, an infection and/or a condition with at least one inflammatory component, and/or any infectious or inflammatory disease, such as a rheumatoid arthritis, a psoriasis, a fibrosis, leprosy, multiple sclerosis, inflammatory bowel disease, or ulcerative colitis or Crohn's disease.

In treating cancer, a traditional antineoplastic agent is contained in the outer lipid vesicle of the nanocell, and an antiangiogenic agent of this invention is loaded into the nanocore. This arrangement allows the antineoplastic agent to be released first and delivered to the tumor before the tumor's blood supply is cut off by the composition of this invention.

The invention also provides multilayered liposomes comprising compounds used to practice this invention, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome used to practice the invention may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles comprising compounds used to practice this invention to deliver a composition of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Liposomes

The compositions and formulations used to practice the invention can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. For example, in one embodiment, compositions and formulations used to practice the invention are delivered by the use of liposomes having rigid lipids having head groups and hydrophobic tails, e.g., as using a polyethyleneglycol-linked lipid having a side chain matching at least a portion the lipid, as described e.g., in US Pat App Pub No. 20080089928. In another embodiment, compositions and formulations used to practice the invention are delivered by the use of amphoteric liposomes comprising a mixture of lipids, e.g., a mixture comprising a cationic amphiphile, an anionic amphiphile and/or neutral amphiphiles, as described e.g., in US Pat App Pub No. 20080088046, or 20080031937. In another embodiment, compositions and formulations used to practice the invention are delivered by the use of liposomes comprising a polyalkylene glycol moiety bonded through a thioether group and an antibody also bonded through a thioether group to the liposome, as described e.g., in US Pat App Pub No. 20080014255. In another embodiment, compositions and formulations used to practice the invention are delivered by the use of liposomes comprising glycerides, glycerophospholipides, glycerophosphinolipids, glycerophosphonolipids, sulfolipids, sphingolipids, phospholipids, isoprenolides, steroids, stearines, sterols and/or carbohydrate containing lipids, as described e.g., in US Pat App Pub No. 20070148220.

Therapeutically Effective Amount and Dose

In alternative embodiment, pharmaceutical compositions and formulations used to practice the invention can be administered for prophylactic and/or therapeutic treatments; for example, the invention provides methods for treating, preventing or ameliorating: a disease or condition associated with dysfunctional cells or blood vessel growth, a retinal age-related macular degeneration, a diabetic retinopathy, a cancer or carcinoma, a glioblastoma, a neuroma, a neuroblastoma, a colon carcinoma, a hemangioma, an infection and/or a condition with at least one inflammatory component, and/or any infectious or inflammatory disease, such as a rheumatoid arthritis, a psoriasis, a fibrosis, leprosy, multiple sclerosis, inflammatory bowel disease, or ulcerative colitis or Crohn's disease. In therapeutic applications, compositions are administered to a subject already suffering from a condition, infection or disease in an amount sufficient to cure, alleviate or partially arrest the clinical manifestations of the condition, infection or disease (e.g., disease or condition associated with dysfunctional blood vessel growth, dysfunctional cell or cancer stem cell growth) and its complications (a "therapeutically effective amount"). In the methods of the invention, a pharmaceutical composition is administered in an amount sufficient to treat (e.g., ameliorate) or prevent a disease or condition associated with dysfunctional blood vessel growth. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

Kits and Instructions

The invention provides kits comprising compositions for practicing the methods of the invention, including instructions for use thereof. In alternative embodiments, the invention provides kits comprising microRNA-103 or anti-microRNA-103. In alternative embodiments, the invention provides kits comprising a composition, product of manufacture, or mixture or culture of cells for practicing a method of the invention; wherein optionally the kit further comprises instructions for practicing a method of the invention.

A number of embodiments of the invention have been described. Nevertheless, it will be understood that various modifications may be made without departing from the spirit and scope of the invention. Accordingly, other embodiments are within the scope of the following claims.

What is claimed is:

1. A method for inhibiting DNA repair enzymes TREX1 and TREX2, or destabilizing a DNA repair response of a cell, or forcing or stimulating a cell to undergo cell cycle arrest or cell death, comprising:
   (a) providing a composition comprising a microRNA-103 (miRNA-103, or miR103) or equivalents thereof, or chemically modified and stabilized forms of miR-103, and/or a FANCF gene expression-inhibiting composition or a FANCF gene expression-inhibiting microRNA or siRNA; and
   (b) administering a sufficient amount of the composition, microRNA-103 or equivalents, and/or a FANCF gene expression-inhibiting composition or a FANCF gene expression-inhibiting microRNA or siRNA, to inhibit DNA repair enzymes TREX1 and TREX2, or destabilize a DNA repair response of a cell, or force or stimulate a cell to undergo cell cycle arrest or cell death.

2. The method of claim 1, wherein the composition comprises a pharmaceutical composition administered in vivo.

3. The method of claim 1, wherein the composition is administered intravenously (IV), or by vessel-targeted nanoparticle or liposome delivery.

4. The method of claim 1, wherein the composition administered to inhibit DNA repair enzymes TREX1 and TREX2, or destabilize a DNA repair response of a cell, or force or stimulate a cell to undergo cell cycle arrest or cell death comprises a microRNA-103 (miRNA-103, or miR103).

5. The method of claim 2, wherein the pharmaceutical composition is formulated for administration parenterally, topically, orally, by local administration, by aerosol or transdermally.

6. The method of claim 2, wherein the pharmaceutical composition is formulated for administration as a lipid, a nanoparticle, a tablet, a capsule or a spray.

7. The method of claim 2, wherein the microRNA-103, the chemically modified or stabilized forms of miR-103, the FANCF gene expression-inhibiting composition or the FANCF gene expression-inhibiting microRNA or siRNA are formulated as a lyophilized microRNA or a lyophilized composition.

8. The method of claim 7, wherein the lyophilized microRNA or lyophilized composition are reconstituted with a diluent.

9. The method of claim 8, wherein the diluent comprises a sterile water or a sterile saline for injection.

10. The method of claim 8, wherein the reconstituted microRNA or composition are administered as a subcutaneous injection or as an intravenous infusion.

11. The method of claim 1, wherein the composition administered to inhibit DNA repair enzymes TREX1 and TREX2, or destabilize a DNA repair response of a cell, or force or stimulate a cell to undergo cell cycle arrest or cell death comprises a FANCF gene expression-inhibiting composition.

12. The method of claim 1, wherein the composition administered to inhibit DNA repair enzymes TREX1 and TREX2, or destabilize a DNA repair response of a cell, or force or stimulate a cell to undergo cell cycle arrest or cell death comprises a FANCF gene expression-inhibiting microRNA or siRNA.

13. The method of claim 1, wherein the composition administered to inhibit DNA repair enzymes TREX1 and TREX2, or destabilize a DNA repair response of a cell, or force or stimulate a cell to undergo cell cycle arrest or cell death comprises a chemically modified and stabilized forms of miR-103.

14. The method of claim 1, wherein the microRNA comprise one or more 5'-end modifications, or a guide strand modification.

15. The method of claim 14, wherein the 5'-stem modification comprises a 2'-modified ribose sugar or a 2'-modified nucleotide.

16. The method of claim 14, wherein the 2'-modified nucleotide comprises a 2'-O-methyl modified nucleotide or a 2'-O-allyl nucleotide.

17. The method of claim 1, wherein the microRNA or siRNA comprise a phosphorothioate linkage or a 2'-O-methyl modification.

18. The method of claim 1, wherein the microRNA or siRNA comprise a sugar-modified nucleoside or a bicyclic sugar moiety.

19. The method of claim 18, wherein the bicyclic sugar moiety comprises a 2 linked biradical group, or the bicyclic sugar moiety is bridged between the 2' and 4' carbon atoms with a biradical group selected from —O—(CH2)x-, —O—CH2-, —O—CH2CH2-, —O—CH(alkyl)-, —NH—(CH2)P—, —N(alkyl)-(CH2)x-, —O—CH(alkyl)-, —(CH(alkyl))-(CH2)x-, —NH—O—(CH2)x-, —N(alkyl)-O—(CH2)x-, or —O—N(alkyl)-(CH2)x-, wherein x is 1, 2, 3, 4 or 5.

20. The method of claim 18, wherein the sugar-modified nucleoside comprises a 4'-thio modified nucleoside.

* * * * *